(12) United States Patent
Hagadorn et al.

(10) Patent No.: US 8,710,163 B2
(45) Date of Patent: *Apr. 29, 2014

(54) PYRIDYLDIAMIDO TRANSITION METAL COMPLEXES, PRODUCTION AND USE THEREOF

(75) Inventors: John R. Hagadorn, Houston, TX (US); Matthew S. Bedoya, Humble, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 253 days.

This patent is subject to a terminal disclaimer.

(21) Appl. No.: 13/207,847

(22) Filed: Aug. 11, 2011

(65) Prior Publication Data

US 2011/0301310 A1 Dec. 8, 2011

Related U.S. Application Data

(63) Continuation-in-part of application No. 13/071,738, filed on Mar. 25, 2011, now Pat. No. 8,394,902, which is a continuation-in-part of application No. 12/180,132, filed on Jul. 25, 2008, now Pat. No. 7,973,116.

(51) Int. Cl.
| | |
|---|---|
| C08F 4/76 | (2006.01) |
| C08F 4/64 | (2006.01) |
| C08F 4/52 | (2006.01) |
| C07F 7/00 | (2006.01) |

(52) U.S. Cl.
USPC ........... 526/172; 526/161; 526/160; 526/170; 526/351; 526/352; 556/51

(58) Field of Classification Search
USPC ................. 526/172, 161, 348, 170, 160, 134; 556/51
See application file for complete search history.

(56) References Cited

U.S. PATENT DOCUMENTS

| | | | |
|---|---|---|---|
| 5,318,935 A | 6/1994 | Canich et al. | |
| 6,103,657 A | 8/2000 | Murray | |
| 6,521,793 B1 | 2/2003 | Guram et al. | |
| 6,610,805 B1 | 8/2003 | Guram et al. | |
| 6,683,141 B1 * | 1/2004 | Gibson et al. | 526/161 |
| 6,750,345 B2 * | 6/2004 | Boussie et al. | 546/10 |
| 6,900,321 B2 | 5/2005 | Boussie et al. | |
| 7,018,949 B2 | 3/2006 | Boussie et al. | |
| 7,041,765 B2 | 5/2006 | Tau et al. | |
| 7,045,583 B2 * | 5/2006 | Kuchta et al. | 526/172 |
| 7,102,006 B2 | 9/2006 | Vogel et al. | |
| 7,164,020 B2 | 1/2007 | Vogel | |
| 7,317,057 B2 * | 1/2008 | Solan et al. | 526/172 |
| 7,425,661 B2 | 9/2008 | McConville et al. | |
| 7,973,116 B2 * | 7/2011 | Hagadorn et al. | 526/172 |
| 8,394,902 B2 * | 3/2013 | Hagadorn et al. | 526/172 |
| 2002/0156279 A1 | 10/2002 | Boussie et al. | |
| 2004/0220050 A1 | 11/2004 | Frazier et al. | |
| 2006/0135722 A1 | 6/2006 | Boussie et al. | |
| 2007/0191607 A1 | 8/2007 | Solan et al. | |
| 2010/0022726 A1 | 1/2010 | Hagadorn et al. | |

FOREIGN PATENT DOCUMENTS

| | | | | |
|---|---|---|---|---|
| JP | 2001-048925 | | 2/2001 | |
| JP | 2001-48925 A | * | 2/2001 | ............. C08F 10/00 |
| WO | WO 2005/095469 | | 10/2005 | |
| WO | WO 2007/067965 | | 6/2007 | |
| WO | WO 2010/037059 | | 4/2010 | |

OTHER PUBLICATIONS

Froese et al., Mechanism of Activation of a Hafnium Pyridyl-Amide Olefin Polymerization Catalyst: Ligand Modification by Monomer, J. Am. Chem. Soc., 2007, vol. 129, No. 25, pp. 7831-7840.
Guérin et al., Synthesis, Structure, and Reactivity of Zirconium Alkyl Complexes Bearing Ancillary Pyridine Diamide Ligands, Organometallics, 1998, vol. 17, No. 23, pp. 5172-5177.

* cited by examiner

*Primary Examiner* — Rip A. Lee
(74) *Attorney, Agent, or Firm* — Catherine L. Bell

(57) ABSTRACT

Pyridyldiamido transition metal complexes are disclosed for use in alkene polymerization.

35 Claims, 1 Drawing Sheet

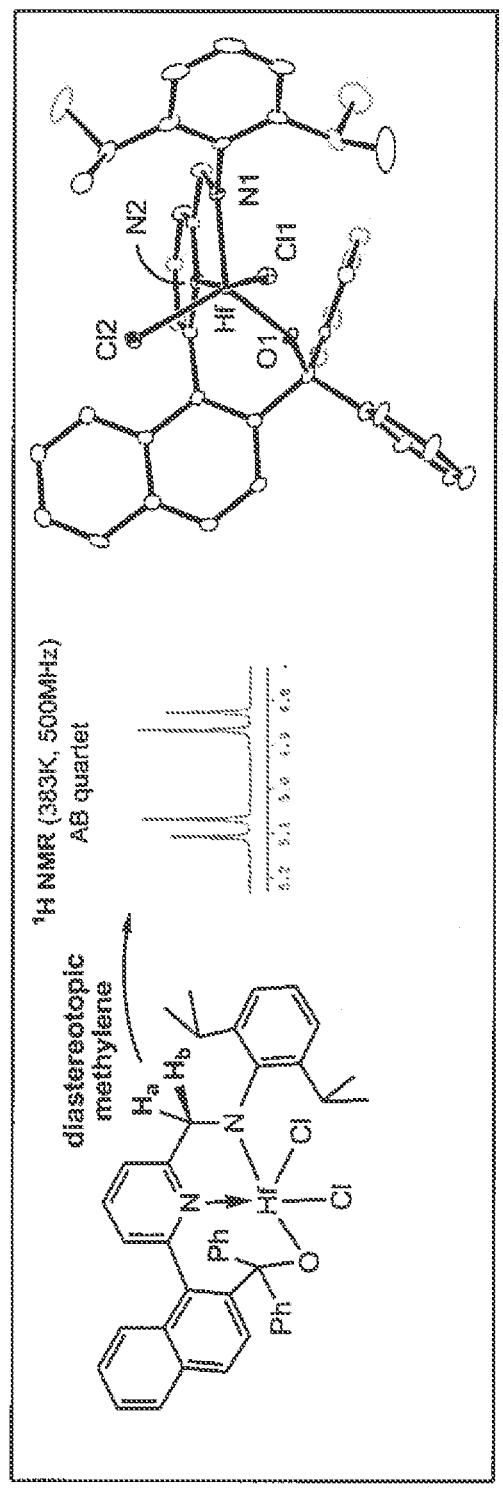

PYRIDYLDIAMIDO TRANSITION METAL COMPLEXES, PRODUCTION AND USE THEREOF

US PRIORITY CLAIM

This application is a continuation-in part of U.S. Ser. No. 13/071,738, filed Mar. 25, 2011 (granted as U.S. Pat. No. 8,394,902), which is a continuation-in-part of 12/180,132, filed Jul. 25, 2008 (granted as U.S. Pat. No. 7,973,116).

FIELD OF INVENTION

The invention relates to pyridyldiamido transition metal complexes and intermediates and processes for use in making such pyridyldiamido complexes. The transition metal complexes may be used as catalysts for alkene polymerization processes.

BACKGROUND OF INVENTION

Pyridyl amines have been used to prepare Group 4 complexes which are useful transition metal components for use in the polymerization of alkenes, see for example U.S. 2002/0142912; U.S. Pat. Nos. 6,900,321; and 6,103,657, where the ligands have been used in complexes in which the ligands are coordinated in a bidentate fashion to the transition metal atom.

WO 2005/095469 shows catalyst compounds that use tridentate ligands through two nitrogen atoms (one amido and one pyridyl) and one oxygen atom.

U.S. 2004/0220050A1 and WO 2007/067965 disclose complexes in which the ligand is coordinated in a tridentate fashion through two nitrogen (one amido and one pyridyl) and one carbon (aryl anion) donors.

A key step in the activation of these complexes is the insertion of an alkene into the metal-aryl bond of the catalyst precursor (Froese, R. D. J. et al., J. Am. Chem. Soc. 2007, 129, pp. 7831-7840) to form an active catalyst that has both five-membered and a seven-membered chelate rings.

WO 2010/037059 discloses pyridine containing amines for use in pharmaceutical applications.

There still is need for adding synthetic routes to widen the range of catalysts complexes that may be prepared and broaden their performance in alkene polymerization. The performance may be varied in respect of the amount of polymer produced per amount of catalyst (generally referred to as the "activity") under the prevailing polymerization conditions; the molecular weight and molecular weight distribution achieved at a given temperature; and the placement of higher alpha-olefins in terms of the degree of stereoregular placement.

SUMMARY OF INVENTION

This invention relates to novel transition metal complexes having tridentate NNN ligands. The ligand may be derived from a neutral ligand precursor or be created in situ in a complex, as will be described. This invention also relates to a pyridyldiamido transition metal complex having the general formula (I), (II), or (III):

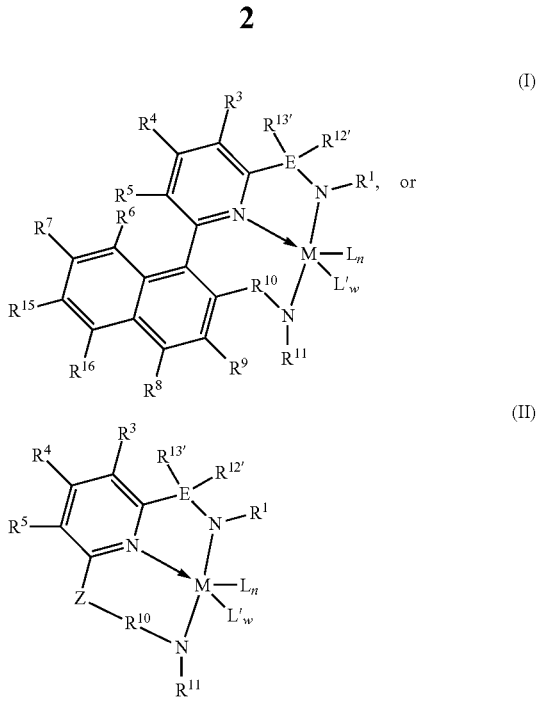

wherein:

M is a Group 3, 4, 5, 6, 7, 8, 9, 10, 11, or 12 metal;

$R^1$ is selected from the group consisting of hydrocarbyls (such as alkyls, aryls), substituted hydrocarbyls (such as heteroaryls), and silyl groups;

$R^{11}$ is selected from the group consisting of substituted 5 or 6 membered aromatic rings;

$R^{10}$ is -E*($R^{12}$)($R^{13}$)—;

E and E* are independently, carbon, silicon, or germanium;

each $R^{12}$ and $R^{13}$ is independently selected from the group consisting of hydrogen, hydrocarbyls (e.g., alkyl and aryl), substituted hydrocarbyls (e.g., heteroaryl), alkoxy, silyl, amino, aryloxy, halogen, and phosphino, $R^{12}$ and $R^{13}$ may be joined to form a saturated, substituted or unsubstituted hydrocarbyl ring, where the ring has 4, 5, 6, or 7 ring carbon atoms and where substitutions on the ring can join to form additional rings, or $R^{12}$ and $R^{13}$ may be joined to form a saturated heterocyclic ring, or a saturated substituted heterocyclic ring where substitutions on the ring can join to form additional rings;

each $R^{12}$* and $R^{13}$* is independently selected from the group consisting of hydrogen, C1 to C5 hydrocarbyls, and substituted C1 to C5 hydrocarbyls;

$R^3$, $R^4$, and $R^5$ are independently selected from the group consisting of hydrogen, hydrocarbyls (e.g., alkyls and aryls), substituted hydrocarbyls (e.g., heteroaryl), alkoxy, aryloxy, halogen, amino, and silyl, and wherein adjacent R groups ($R^3$ & $R^4$ and/or $R^4$ & $R^5$) may be joined to form a substituted or unsubstituted hydrocarbyl or heterocyclic ring, where the ring has 5, 6, 7, or 8 ring atoms and where substitutions on the ring can join to form additional rings;

$R^6$, $R^7$, $R^8$, $R^9$, $R^{15}$, and $R^{16}$ are independently selected from the group consisting of hydrogen, hydrocarbyls, substituted hydrocarbyls, alkoxy, halogen, amino, and silyl, and wherein adjacent R groups ($R^6$ & $R^7$, and/or $R^7$ & $R^{15}$, and/or $R^{16}$ & $R^{15}$, and/or $R^8$ & $R^9$) may be joined to form a saturated, substituted or unsubstituted hydrocarbyl or heterocyclic ring, where the ring has 5, 6, 7, or 8 ring carbon atoms and where substitutions on the ring can join to form additional rings;

L is an anionic leaving group, where the L groups may be the same or different and any two L groups may be linked to form a dianionic leaving group;

n is 0, 1, 2, 3, or 4;

L' is neutral Lewis base;

w is 0, 1, 2, 3, or 4;

Z is —$(R^{14*})_p$-Q-J$(R^{15*})_q$—;

Q is C, O, N, or Si;

J is C or Si;

$R^{14*}$ and $R^{15*}$ are independently selected from the group consisting of hydrogen, hydrocarbyls, and substituted hydrocarbyls, (preferably hydrogen and alkyls), and wherein adjacent $R^{14*}$ and $R^{15*}$ groups may be joined to form an aromatic or saturated, substituted or unsubstituted hydrocarbyl ring, where the ring has 5, 6, 7, or 8 ring carbon atoms and where substitutions on the ring can join to form additional rings;

p is 1 or 2; and q is 1 or 2.

This invention further relates to process to make the above complex, process to make intermediates for the above complex and methods to polymerize olefins using the above complex.

BRIEF DESCRIPTION OF THE DRAWINGS

FIG. 1 is an illustration of the diastereotopic methylene for a composition of the invention.

DETAILED DESCRIPTION

The specification describes transition metal complexes. The term complex is used to describe molecules in which an ancillary ligand is coordinated to a central transition metal atom. The ligand is bulky and stably bonded to the transition metal so as to maintain its influence during use of the catalyst, such as polymerization. The ligand may be coordinated to the transition metal by covalent bond and/or electron donation coordination or intermediate bonds. The transition metal complexes are generally subjected to activation to perform their polymerization or oligomerization function using an activator which is believed to create a cation as a result of the removal of an anionic group, often referred to as a leaving group, from the transition metal.

As used herein, the numbering scheme for the Periodic Table groups is the new notation as set out in Chemical and Engineering News, 63(5), 27 (1985).

The following abbreviations are used throughout this specification: Me is methyl, Ph is phenyl, Et is ethyl, Pr is propyl, iPr is isopropyl, n-Pr is normal propyl, Bu is butyl, iBu is isobutyl, tBu is tertiary butyl, p-tBu is para-tertiary butyl, nBu is normal butyl, TMS is trimethylsilyl, TIBAL is triisobutylaluminum, TNOAL is triisobutyl n-octylaluminum, MAO is methylalumoxane, pMe is para-methyl, Ar* is 2,6-diisopropylaryl, Ph is phenyl, Bn is benzyl (i.e., $CH_2Ph$), THF (also referred to as thf) is tetrahydrofuran, RT is room temperature, tol is toluene, EtOAc is ethyl acetate, and Cy is cyclohexyl.

The term "substituted" means that a hydrogen has been replaced with a heteroatom or a hydrocarbyl group. For example, methyl-cyclopentadiene is substituted with a methyl group.

The terms "hydrocarbyl radical," "hydrocarbyl" and "hydrocarbyl group" are used interchangeably throughout this document. Likewise the terms "group", "radical", and "substituent" are also used interchangeably in this document. For purposes of this disclosure, "hydrocarbyl radical" is defined to be $C_1$-$C_{100}$ radicals, that may be linear, branched, or cyclic, and when cyclic, aromatic or non-aromatic.

Substituted hydrocarbyl radicals are radicals in which at-least one hydrogen atom of the hydrocarbyl radical has been substituted with at least one functional group such as $NR*_2$, $OR*$, $SeR*$, $TeR*$, $PR*_2$, $AsR*_2$, $SbR*_2$, $SR*$, $BR*_2$, $SiR*_3$, $GeR*_3$, $SnR*_3$, $PbR*_3$, and the like, or where at least one heteroatom has been inserted within a hydrocarbyl ring.

The term "catalyst system" is defined to mean a complex/activator pair. When "catalyst system" is used to describe such a pair before activation, it means the unactivated catalyst complex (precatalyst) together with an activator and, optionally, a co-activator. When it is used to describe such a pair after activation, it means the activated complex and the activator or other charge-balancing moiety. The transition metal compound may be neutral as in a precatalyst, or a charged species with a counter ion as in an activated catalyst system.

Complex, as used herein, is also often referred to as catalyst precursor, precatalyst, catalyst, catalyst compound, transition metal compound, or transition metal complex. These words are used interchangeably. Activator and cocatalyst are also used interchangeably.

A scavenger is a compound that is typically added to facilitate polymerization by scavenging impurities. Some scavengers may also act as activators and may be referred to as co-activators. A co-activator, that is not a scavenger, may also be used in conjunction with an activator in order to form an active catalyst. In some embodiments a co-activator can be pre-mixed with the transition metal compound to form an alkylated transition metal compound.

Noncoordinating anion (NCA) is defined to mean an anion either that does not coordinate to the catalyst metal cation or that does coordinate to the metal cation, but only weakly. The term NCA is also defined to include multicomponent NCA-containing activators, such as N,N-dimethylanilinium tetrakis(pentafluorophenyl)borate, that contain an acidic cationic group and the non-coordinating anion. The term NCA is also defined to include neutral Lewis acids, such as tris(pentafluorophenyl)boron, that can react with a catalyst to form an activated species by abstraction of an anionic group. An NCA coordinates weakly enough that a neutral Lewis base, such as an olefinically or acetylenically unsaturated monomer can displace it from the catalyst center. Any metal or metalloid that can form a compatible, weakly coordinating complex may be used or contained in the noncoordinating anion. Suitable metals include, but are not limited to, aluminum, gold, and platinum. Suitable metalloids include, but are not limited to, boron, aluminum, phosphorus, and silicon. A stoichiometric activator can be either neutral or ionic. The terms ionic activator, and stoichiometric ionic activator can be used interchangeably. Likewise, the terms neutral stoichiometric activator, and Lewis acid activator can be used interchangeably. The term non-coordinating anion includes neutral stoichiometric activators, ionic stoichiometric activators, ionic activators, and Lewis acid activators.

When a polymer or oligomer is referred to as comprising an olefin, the olefin present in the polymer or oligomer is the polymerized or oligomerized form of the olefin (for example polyethylene is made of units derived from ethylene). An oligomer is defined to be compositions having 2-50 monomer units. A polymer is defined to be compositions having 51 or more monomer units.

A higher α-olefin is defined to be an a-olefin having 4 or more carbon atoms.

Unless otherwise noted, all molecular weights units (e.g., Mw, Mn, Mz) are g/mol.

Unless otherwise noted all melting points ($T_m$) are DSC second melt.

A "ring carbon atom" is a carbon atom that is part of a cyclic ring structure. By this definition, a benzyl group has six ring carbon atoms and para-methylstyrene also has six ring carbon atoms.

The term "aryl" or "aryl group" means a six carbon aromatic ring and the substituted variants thereof, including but not limited to, phenyl, 2-methyl-phenyl, xylyl, 4-bromo-xylyl. Likewise heteroaryl means an aryl group where a ring carbon atom (or two or thee ring carbon atoms) has been replaced with a heteroatom, preferably N, O, or S.

The term "ring atom" means an atom that is part of a cyclic ring structure. By this definition, a benzyl group has six ring atoms and tetrahydrofuran has 5 ring atoms.

A heterocyclic ring is a ring having a heteroatom in the ring structure as opposed to a heteroatom substituted ring where a hydrogen on a ring atom is replaced with a heteroatom. For example, tetrahydrofuran is a heterocyclic ring and 4-N,N-dimethylamino-phenyl is a heteroatom substituted ring.

As used herein, the term "aromatic" also refers to pseudoaromatic heterocycles which are heterocyclic substituents that have similar properties and structures (nearly planar) to aromatic heterocyclic ligands, but are not by definition aromatic; likewise the term aromatic also refers to substituted aromatics.

The term "continuous" means a system that operates without interruption or cessation. For example a continuous process to produce a polymer would be one where the reactants are continually introduced into one or more reactors and polymer product is continually withdrawn.

A solution polymerization means a polymerization process in which the polymer is dissolved in a liquid polymerization medium, such as an inert solvent or monomer(s) or their blends. A solution polymerization is typically homogeneous. A homogeneous polymerization is one where the polymer product is dissolved in the polymerization medium. Such systems are preferably not turbid as described in J. Vladimir Oliveira, C. Dariva and J. C. Pinto, Ind. Eng, Chem. Res. 29, 2000, 4627.

A bulk polymerization means a polymerization process in which the monomers and/or comonomers being polymerized are used as a solvent or diluent using little or no inert solvent as a solvent or diluent. A small faction of inert solvent might be used as a carrier for catalyst and scavenger. A bulk polymerization system contains less than 25 wt % of inert solvent or diluent, preferably less than 10 wt %, preferably less than 1 wt %, preferably 0 wt %.

In a first aspect of the invention, there is provided a pyridyldiamido transition metal complex (optionally, for use in alkene polymerization) having the general formula: (I) or (II):

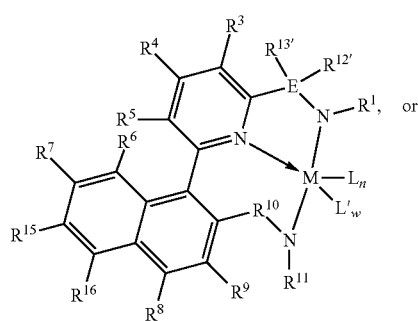

(I)

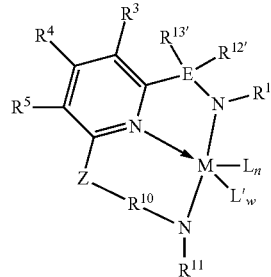

(II)

wherein:
M is a Group 3, 4, 5, 6, 7, 8, 9, 10, 11, or 12 metal (preferably a Group 4 metal, preferably Ti, Zr or Hf, preferably Hf or Zr, preferably Hf);
$R^1$ is selected from the group consisting of hydrocarbyls, substituted hydrocarbyls, and silyl groups (preferably alkyl, aryl, heteroaryl, and silyl groups);
$R^{11}$ is selected from the group consisting of substituted 5 or 6 (preferably 6) membered aromatic rings, (such as substituted 5 or 6 membered rings where the ring atoms are carbon or heterocyclic rings having 1, 2 or 3 heteroatoms in the ring (such as N, O or S)) where the substitution is a hydrocarbyl group, a heteroatom, or a heteroatom containing group, preferably $R^{11}$ is a substituted aryl group, preferably a 2,6 or 2,4,6 substituted aryl group;
$R^{10}$ is -E*($R^{12}$)($R^{13}$)— (preferably $R^{10}$ is $CH_2$, preferably $R^{12}$ and $R^{13}$ are the same);
E and E* are, independently, carbon, silicon, or germanium (preferably carbon or silicon, preferably carbon);
each $R^{12}$ and $R^{13}$ is independently selected from the group consisting of hydrogen, hydrocarbyl, and substituted hydrocarbyl, alkoxy, silyl, amino, aryloxy, halogen, and phosphino (preferably hydrogen, alkyl, aryl, alkoxy, silyl, amino, aryloxy, heteroaryl, halogen, and phosphino), $R^{12}$ and $R^{13}$ may be joined to form a saturated, substituted or unsubstituted hydrocarbyl ring, where the ring has 4, 5, 6, or 7 ring carbon atoms and where substitutions on the ring can join to form additional rings, or $R^{12}$ and $R^{13}$ may be joined to form a saturated heterocyclic ring, or a saturated substituted heterocyclic ring where substitutions on the ring can join to form additional rings;
each $R^{12}*$ and $R^{13}*$ is independently selected from the group consisting of hydrogen, C1 to C5 hydrocarbyls, substituted C1 to C5 hydrocarbyls, preferably hydrogen, methyl, ethyl, propyl, butyl, pentyl;
$R^3$, $R^4$, and $R^5$ are independently selected from the group consisting of hydrogen, hydrocarbyls, substituted hydrocarbyls, alkoxy, aryloxy, halogen, amino, and silyl, (preferably hydrogen, alkyl, alkoxy, aryloxy, halogen, amino, silyl, and aryl), and wherein adjacent R groups ($R^3$ & $R^4$ and/or $R^4$ & $R^5$) may be joined to form a substituted or unsubstituted hydrocarbyl or heterocyclic ring, where the ring has 5, 6, 7, or 8 ring atoms and where substitutions on the ring can join to form additional rings;
$R^6$, $R^7$, $R^8$, $R^9$, $R^{15}$, and $R^{16}$ are independently selected from the group consisting of hydrogen, hydrocarbyls, substituted hydrocarbyls, alkoxy, halogen, amino, and silyl, and the pairs of positions, and wherein adjacent R groups ($R^6$ & $R^7$, and/or $R^7$ & $R^{15}$, and/or $R^{16}$ & $R^{15}$, and/or $R^8$ & $R^9$) may be joined to form a saturated, substituted or unsubstituted hydrocarbyl or heterocyclic ring, where the ring has 5, 6, 7, or 8 ring carbon atoms and where substitutions on the ring can join to form additional rings;

L is an anionic leaving group, where the L groups may be the same or different and any two L groups may be linked to form a dianionic leaving group;

n is 0, 1, 2, 3, or 4;

L' is neutral Lewis base;

w is 0, 1, 2, 3, or 4;

Z is —$(R^{14*})_p$Q-J$(R^{15*})_q$— where Q or J is bonded to $R^{10}$;

J is C or Si, preferably C;

Q is C, O, N, or Si, preferably C (preferably both J and Q are C);

$R^{14*}$ and $R^{15*}$ are independently selected from the group consisting of hydrogen, hydrocarbyls, and substituted hydrocarbyls, (preferably hydrogen and alkyls), and wherein adjacent $R^{14*}$ and $R^{15*}$ groups may be joined to form an aromatic or saturated, substituted or unsubstituted hydrocarbyl ring, where the ring has 5, 6, 7, or 8 ring carbon atoms and where substitutions on the ring can join to form additional rings;

p is 1 or 2; and q is 1 or 2.

Preferably the R groups above and other R groups mentioned hereafter, contain up to 30 carbon atoms, preferably no more than 30 carbon atoms, especially from 2 to 20 carbon atoms.

Preferably M is Ti, Zr, or Hf and/or E and/or E* is carbon, with Zr or Hf based complexes being especially preferred.

In a preferred embodiment, $R^1$ is selected from phenyl groups that are variously substituted with between zero to five substituents that include F, Cl, Br, I, $CF_3$, $NO_2$, alkoxy, dialkylamino, aryl, and alkyl groups with between one to ten carbons.

In a preferred embodiment, $R^{11}$ is selected from aryl groups that are variously substituted with between zero to five substituents that include F, Cl, Br, I, $CF_3$, $NO_2$, alkoxy, dialkylamino, aryl, and alkyl groups with between one to ten carbons, preferably $R^{11}$ is 2,6 or 2,4,6 substituted aryl, preferably where the substituents are methyl, ethyl, methoxy, propyl, tert-butyl, butyl, isopropyl, pentyl, hexyl, isobutyl, chloro, fluoro, bromo, iodo, trimethylsilyl, or triethylsilyl. In a preferred embodiment, $R^{11}$ is 2,4,6-trimethylphenyl, 2,6-dimethylphenyl, 2,6-diethylphenyl, 2,6-diisobutylphenyl, 2,5-dimethylphenyl, 2,4,5-trimethylphenyl, 2,3,4,5,6-pentamethylphenyl, 2,6-diisopropylphenyl, or 2,4,6-triisopropylphenyl.

In a preferred embodiment, each L may be independently selected from halide, alkyl, aryl, alkoxy, amido, hydrido, phenoxy, hydroxy, silyl, allyl, alkenyl, triflate, alkylsulfonate, arylsulfonate, and alkynyl. The selection of the leaving groups depends on the synthesis route adopted for arriving at the complex and may be changed by additional reactions to suit the later activation method in polymerization. For example, alkyl is preferred when using non-coordinating anions such as N,N-dimethylanilinium tetrakis(pentafluorophenyl)-borate or tris(pentafluorophenyl)borane. In another embodiment, two L groups may be linked to form a dianionic leaving group, for example, oxalate.

In another embodiment, each L' is independently selected from the group consisting of ethers, thio-ethers, amines, nitriles, imines, pyridines, and phosphines, preferably ethers.

In any embodiment described herein, M is preferably a Group 4 metal, preferably Zr or Hf.

In any embodiment described herein, E and or E* is preferably carbon.

In any embodiment described herein, one of $R^{12*}$ and $R^{13*}$ is preferably hydrogen. In any embodiment described herein, $R^{12*}$ and $R^{13*}$ are not benzyl.

In any embodiment described herein, $R^{10}$ is $CH_2$.

In any embodiment described herein, preferably $R^{12}$ and $R^{13}$ are the same.

In any embodiment described herein, $R^{10}$ is represented by the formula:

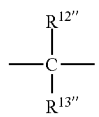

In any embodiment described herein, $R^{12''}$ is hydrogen, alkyl, aryl, or halogen; and $R^{13''}$ is hydrogen, alkyl, aryl, or halogen, preferably $R^{12''}$ and $R^{13''}$ are the same.

Preferably, in any embodiment described herein, $R^{12*}$ and $R^{13*}$ are the same.

In any embodiment described herein, $R^6$, $R^7$, $R^8$, $R^9$, $R^{15}$, and $R^{16}$ may be, independently, selected from the group consisting of hydrogen, hydrocarbyls, substituted hydrocarbyls, alkoxy, halogen, amino, and silyl.

In any embodiment described herein, $R^1$, $R^3$, $R^4$, $R^5$, and $R^{11}$ may each contain no more than 30 carbon atoms, preferably $R^1$, $R^3$, $R^4$, $R^5$, $R^6$, $R^7$, $R^8$, $R^9$, and $R^{15}$ each contain no more than 30 carbon atoms.

In any embodiment described herein, E is carbon and $R^1$ is selected from phenyl groups that are substituted with 0, 1, 2, 3, 4, or 5 substituents selected from the group consisting of F, Cl, Br, I, $CF_3$, $NO_2$, alkoxy, dialkylamino, hydrocarbyl, and substituted hydrocarbyls groups with from one to ten carbons.

In a preferred embodiment, the pyridyldiamido transition metal complex is represented by the Formula (I) or (II) above and at least one of $R^{12*}$ and $R^{13*}$ is a group containing from 1 to 5 (preferably 1 to 4, preferably 1 to 3) carbons.

In a preferred embodiment, the pyridyldiamido transition metal complex is represented by the Formula (I) or (II) above, $R^{12}$ is H, $R^{13}$ is a group containing between 1 to 100 (preferably. 6 to 40, preferably 7 to 30) carbons, M is a Group 4 metal, preferably Zr or Hf, E is carbon, $R^{12''}$ and $R^{13''}$ are the same, preferably $R^{10}$ is $CH_2$.

In a preferred embodiment, the pyridyldiamido transition metal complex is represented by the Formula (I) above, and M is a Group 4 metal preferably Zr or Hf, preferably Hf.

In a preferred embodiment, the pyridyldiamido transition metal complex is represented by the Formula (II) above, and M is a Group 4 metal preferably Zr or Hf, preferably Hf.

In a preferred embodiment, the pyridyldiamido transition metal complex is represented by the Formula (II) above, and $R^{10}$ is $CH_2$.

In a preferred embodiment, the pyridyldiamido transition metal complex is represented by the Formula (I) or (II) and both $R^{12*}$ and $R^{13*}$ are a $C_1$ to $C_5$ alkyl group, alternately methyl, ethyl, propyl, butyl, pentyl or an isomer thereof.

In another preferred embodiment, the pyridyldiamido transition metal complex is represented by the Formula (I) or (II) and $R^{12*}$ and $R^{13*}$ are hydrogen, E is C, and E* is C or Si.

In another aspect of the invention, there are provided various processes for synthesizing the complexes described herein.

The pyridyl diamine ligands described herein are generally prepared in multiple steps. One step involves the preparation of an amine-containing "linker" group where the linker is typically a boronic acid ester of an aryl methyl amine or substituted amine. This amine-containing linker may be prepared from an aryl-methyl boronic ester in two steps, the first of which involves the conversion of the methyl group to a halo-methyl group by free radical halogenation in unreactive solvents (e.g., $CCl_4$, benzene). The second step then involves reaction of this halo-methyl group containing species with an amine or protected amine or deprotonated protected amine to yield an amine-containing linker. This amine-containing linker is then coupled with a suitable pyridine containing species, such as 6-bromo-2-pyridinecarboxaldehyde. This coupling step typically uses a metal catalyst (e.g., $Pd(PPh_3)_4$) in less than 5 mol % loading. Following this coupling step, the new derivative, which can be described as amine-linker-pyridine-aldehyde, is then reacted with a second amine to produce the imine derivative amine-linker-pyridine-imine in a condensation reaction. This can then be reduced to the pyridyl diamine ligand by reaction with a suitable aryl anion, alkyl anion, or hydride source. This reaction is generally performed in etherial solvents at temperatures between –100° C. and 50° C. when aryllithium or alkyllithium reagents are employed. This reaction is generally performed in methanol at reflux when sodium cyanoborohydride is employed.

The preparation of pyridyl diamide metal complexes from pyridyl diamines may be accomplished using typical protonolysis and methylation reactions. In the protonolysis reaction the pyridyl diamine is reacted with a suitable metal reactant to produce a pyridyldiamide metal complex. A suitable metal reactant will feature a basic leaving group that will accept a proton from the pyridiyl diamine and then generally depart and be removed from the product. Suitable metal reactants include, but are not limited to, $HfBn_4$ (Bn=$CH_2Ph$), $ZrBn_4$, $TiBn_4$, $ZrBn_2Cl_2(OEt_2)$, $HfBn_2Cl_2(OEt_2)_2$, $Zr(NMe_2)_2Cl_2$(dimethoxyethane), $Hf(NMe_2)_2Cl_2$ (dimethoxyethane), $Hf(NMe_2)_4$, and $Hf(NEt_2)_4$. Pyridyldiamide metal complexes that contain metal-chloride groups, such as the PDA dichloride complex in Scheme 1 below, can be alkylated by reaction with an appropriate organometallic reagent. Suitable reagents include organolithium and organomagnesium, and Grignard reagents. The alkylations are generally performed in etherial or hydrocarbon solvents or solvent mixtures at temperatures typically ranging from –100° C. to 50° C.

Scheme 1

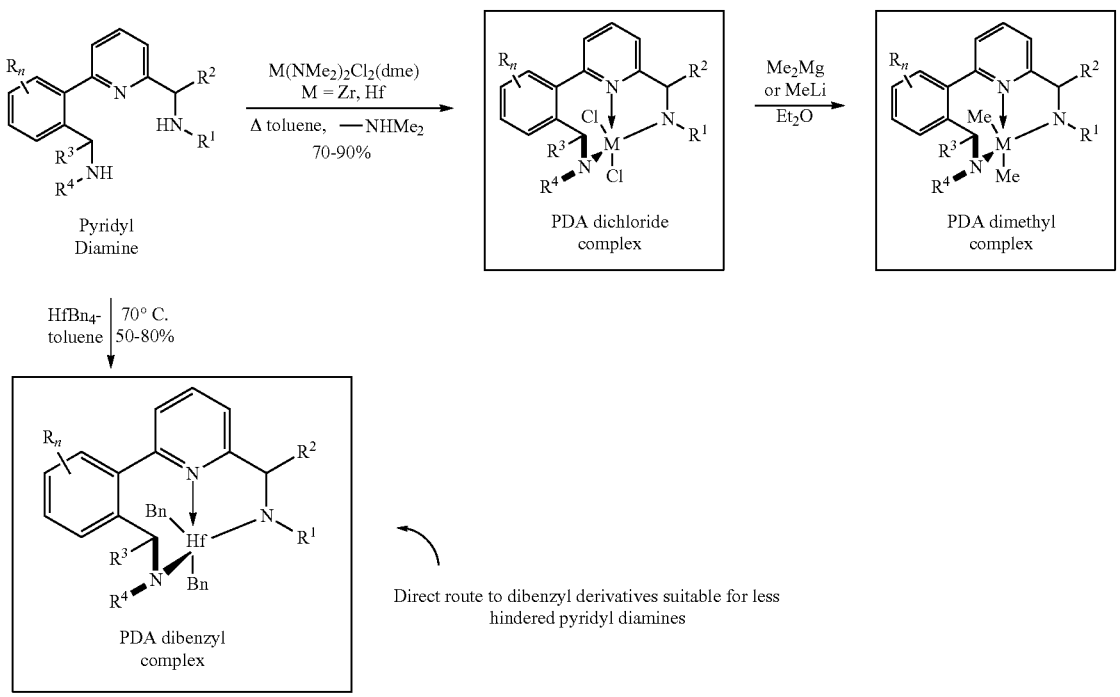

Direct route to dibenzyl derivatives suitable for less hindered pyridyl diamines where in Scheme 1, R, $R^1$, $R^2$, $R^3$, $R^4$ are independently selected from the group consisting of H, hydrocarbyls (such as alkyls, aryls), substituted hydrocarbyls (such as heteroaryls), and silyl groups, and $R_n$ indicates hydrogen, hydrocarbyls, or substituted hydrocarbyls, which may be joined to form polycyclic aromatic ring and n is 1, 2, 3, or 4.

Another route to pyridyl diamide and other complexes of interest as catalysts involves the insertion of an unsaturated molecule into a covalent metal-carbon bond where the covalently bonded group is part of a multidentate ligand structure, such as that described by Boussie et al. in U.S. Pat. No. 6,750,345. The unsaturated molecule will generally have a carbon-X double or triple bond where X is a group 14 or group 15 or group 16 element. Examples of unsaturated molecules include alkenes, alkynes, imines, nitriles, ketones, aldehydes, amides, formamides, carbon dioxide, isocyanates, thioisocyanates, and carbodiimides. Examples showing the insertion reactions involving benzophenone and N,N-dimethylformamide are below.

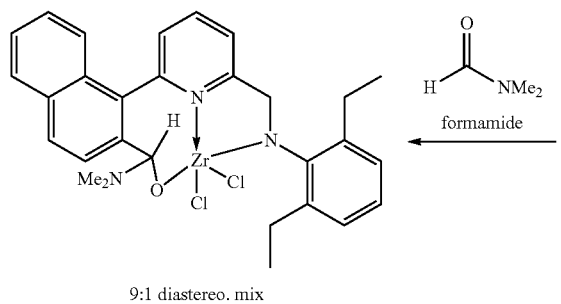

9:1 diastereo. mix

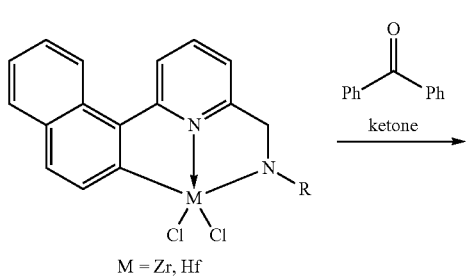

M = Zr, Hf

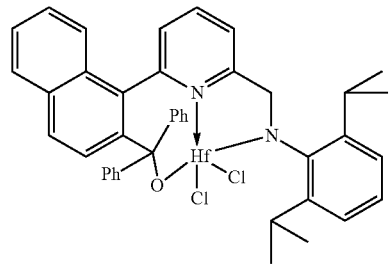

III

Pyridyl diamide complexes may have fluxional structures in solution. This fluxional process may be used to develop "fluxional catalysts", which can be used to produce polymeric products containing blocky structures. A polyolefin molecule with a blocky structure has a non-homogeneous compositional and/or stereochemical distribution of monomers along the polymeric chain. Our studies indicate that the above described fluxionality is fastest for Group 4 pyridyl diamide (PDA) complexes of the general formula (PDA)MX$_2$, where X is alkyl, the PDA ligand lacks substitution at the R$^{10}$ position (based on Formula (III) described herein), and Z is a benzenyl (i.e., C$_6$H$_4$) group. Substitution of the PDA ligand at the R$^{10}$ position slows down the fluxionality a modest amount. Changing the X groups to halide slows down the fluxionality a larger amount. Changing Z to naphthalenyl (i.e., C$_{10}$H$_6$) stops the fluxionality. One method for controlling the fluxionality in these systems would be to use a sub-stoichiometric amount of activator to form a mixture of activated and unactivated species. Of the two, the unactivated species would be expected to undergo relatively fast fluxionality. Thus this would provide a mechanism to produce blocky polyolefins when this system is employed in the presence of, or in the absence of, Group 12 or 13 organometallics (e.g., ZnEt$_2$, AlEt$_3$) that can facilitate polymeryl chain transfer.

Activators

After the complexes have been synthesized, catalyst systems may be formed by combining them with activators in any manner known from the literature including by supporting them for use in slurry or gas phase polymerization. The catalyst systems may also be added to or generated in solution polymerization or bulk polymerization (in the monomer). The catalyst system typically comprises a complex as described above and an activator such as alumoxane or a non-coordinating anion. Activation may be performed using alumoxane solution including methyl alumoxane, referred to as MAO, as well as modified MAO, referred to herein as MMAO, containing some higher alkyl groups to improve the solubility. Particularly useful MAO can be purchased from Albemarle, typically in a 10 wt % solution in toluene. The catalyst system employed in the present invention preferably uses an activator selected from alumoxanes, such as methyl alumoxane, modified methyl alumoxane, ethyl alumoxane, iso-butyl alumoxane, and the like.

When an alumoxane or modified alumoxane is used, the complex-to-activator molar ratio is from about 1:3000 to 10:1; alternatively 1:2000 to 10:1; alternatively 1:1000 to 10:1; alternatively, 1:500 to 1:1; alternatively 1:300 to 1:1; alternatively 1:200 to 1:1; alternatively 1:100 to 1:1; alternatively 1:50 to 1:1; alternatively 1:10 to 1:1. When the activator is an alumoxane (modified or unmodified), some embodiments select the maximum amount of activator at a 5000-fold molar excess over the catalyst precursor (per metal catalytic site). The preferred minimum activator-to-complex ratio is 1:1 molar ratio.

Activation may also be performed using non-coordinating anions, referred to as NCA's, of the type described in EP 277 003 A1 and EP 277 004 A1. NCA may be added in the form of an ion pair using, for example, [DMAH]$^+$ [NCA]$^-$ in which the N,N-dimethylanilinium (DMAH) cation reacts with a basic leaving group on the transition metal complex to form a transition metal complex cation and [NCA]$^-$. The cation in the precursor may, alternatively be trityl. Alternatively, the transition metal complex may be reacted with a neutral NCA precursor, such as B(C$_6$F$_5$)$_3$, which abstracts an anionic group from the complex to form an activated species. Useful activators include N,N-dimethylanilinium tetrakis (pentafluorophenyl)borate (i.e., [PhNMe$_2$H]B(C$_6$F$_5$)$_4$) and N,N-dimethylanilinium tetrakis (heptafluoronaphthyl)borate, where Ph is phenyl, and Me is methyl.

Additionally preferred activators useful herein include those described in U.S. Pat. No. 7,247,687 at column 169, line 50 to column 174, line 43, particularly column 172, line 24 to column 173, line 53.

When an NCA (such as an ionic or neutral stoichiometric activator) is used, the complex-to-activator molar ratio is typically from 1:10 to 1:1; 1:10 to 10:1; 1:10 to 2:1; 1:10 to 3:1; 1:10 to 5:1; 1:2 to 1.2:1; 1:2 to 10:1; 1:2 to 2:1; 1:2 to 3:1; 1:2 to 5:1; 1:3 to 1.2:1; 1:3 to 10:1; 1:3 to 2:1; 1:3 to 3:1; 1:3 to 5:1; 1:5 to 1:1; 1:5 to 10:1; 1:5 to 2:1; 1:5 to 3:1; 1:5 to 5:1; 1:1 to 1:1.2.

Alternately a co-activator, such as a group 1, 2, or 13 organometallic species (e.g., an alkyl aluminum compound such as tri-n-octyl aluminum), may also be used in the catalyst system herein. The complex-to-co-activator molar ratio is from 1:100 to 100:1; 1:75 to 75:1; 1:50 to 50:1; 1:25 to 25:1; 1:15 to 15:1; 1:10 to 10:1; 1:5 to 5:1; 1:2 to 2:1; 1:100 to 1:1; 1:75 to 1:1; 1:50 to 1:1; 1:25 to 1:1; 1:15 to 1:1; 1:10 to 1:1; 1:5 to 1:1; 1:2 to 1:1; 1:10 to 2:1.

In a preferred embodiment, boron containing NCA activators represented by the formula below can be used:

$$Z_d^+(A^{d-})$$

where: Z is (L-H) or a reducible Lewis acid; L is a neutral Lewis base; H is hydrogen; (L-H) is a Bronsted acid; $A^{d-}$ is a boron containing non-coordinating anion having the charge d−; d is 1, 2, or 3. The cation component, $Z_d^+$ may include Bronsted acids such as protons or protonated Lewis bases or reducible Lewis acids capable of protonating or abstracting a moiety, such as an alkyl or aryl, from the bulky ligand metallocene containing transition metal catalyst precursor, resulting in a cationic transition metal species. The activating cation $Z_d^+$ may also be a moiety such as silver, tropylium, carboniums, ferroceniums and mixtures, preferably carboniums and ferroceniums. Most preferably $Z_d^+$ is triphenyl carbonium. Preferred reducible Lewis acids can be any triaryl carbonium (where the aryl can be substituted or unsubstituted, such as those represented by the formula: $(Ar_3C^+)$, where Ar is aryl or aryl substituted with a heteroatom, a $C_1$ to $C_{40}$ hydrocarbyl, or a substituted C1 to C40 hydrocarbyl), preferably the reducible Lewis acids in formula (14) above as "Z" include those represented by the formula: $(Ph_3C)$, where Ph is a substituted or unsubstituted phenyl, preferably substituted with $C_1$ to $C_{40}$ hydrocarbyls or substituted a $C_1$ to $C_{40}$ hydrocarbyls, preferably $C_1$ to $C_{20}$ alkyls or aromatics or substituted $C_1$ to $C_{20}$ alkyls or aromatics, preferably Z is a triphenylcarbonium.

When $Z_d^+$ is the activating cation $(L-H)_d^+$, it is preferably a Bronsted acid, capable of donating a proton to the transition metal catalytic precursor resulting in a transition metal cation, including ammoniums, oxoniums, phosphoniums, silyliums, and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxomiuns from ethers such as dimethyl ether diethyl ether, tetrahydrofuran and dioxane, sulfoniums from thioethers, such as diethyl thioethers, tetrahydrothiophene, and mixtures thereof.

The anion component $A^{d-}$ includes those having the formula $[M^{k+}Q_n]^{d-}$ wherein k is 1, 2, or 3; n is 1, 2, 3, 4, 5, or 6 (preferably 1, 2, 3, or 4); n−k=d; M is an element selected from Group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than 1 occurrence is Q a halide. Preferably, each Q is a fluorinated hydrocarbyl group having 1 to 20 carbon atoms, more preferably each Q is a fluorinated aryl group, and most preferably each Q is a pentafluoryl aryl group. Examples of suitable $A^{d-}$ also include diboron compounds as disclosed in U.S. Pat. No. 5,447,895, which is fully incorporated herein by reference.

Illustrative, but not limiting examples of boron compounds which may be used as an activating cocatalyst are the compounds described as (and particularly those specifically listed as) activators in U.S. Ser. No. 61/494,730, filed Jun. 8, 2011, which is incorporated by reference herein.

Most preferably, the ionic stoichiometric activator $Z_d^+$ $(A^{d-})$ is one or more of N,N-dimethylanilinium tetra(perfluorophenyl)borate, N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, or triphenylcarbenium tetra(perfluorophenyl)borate.

Bulky activators are also useful herein as NCAs. "Bulky activator" as used herein refers to anionic activators represented by the formula:

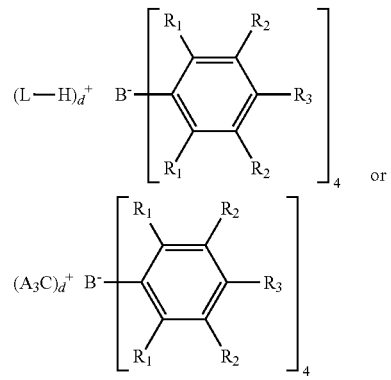

where:
each $R_1$ is, independently, a halide, preferably a fluoride;
Ar is substituted or unsubstituted aryl group (preferably a substituted or unsubstituted phenyl), preferably substituted with $C_1$ to $C_{40}$ hydrocarbyls, preferably $C_1$ to $C_{20}$ alkyls or aromatics;
each $R_2$ is, independently, a halide, a $C_6$ to $C_{20}$ substituted aromatic hydrocarbyl group or a siloxy group of the formula —O—Si—$R_a$, where $R_a$ is a $C_1$ to $C_{20}$ hydrocarbyl or hydrocarbylsilyl group (preferably $R_2$ is a fluoride or a perfluorinated phenyl group);
each $R_3$ is a halide, $C_6$ to $C_{20}$ substituted aromatic hydrocarbyl group or a siloxy group of the formula —O—Si—$R_a$, where $R_a$ is a $C_1$ to $C_{20}$ hydrocarbyl or hydrocarbylsilyl group (preferably $R_3$ is a fluoride or a $C_6$ perfluorinated aromatic hydrocarbyl group); wherein $R_2$ and $R_3$ can form one or more saturated or unsaturated, substituted or unsubstituted rings (preferably $R_2$ and $R_3$ form a perfluorinated phenyl ring); and L is a neutral Lewis base; $(L-H)^+$ is a Bronsted acid; d is 1, 2, or 3;
wherein the anion has a molecular weight of greater than 1020 g/mol;
wherein at least three of the substituents on the B atom each have a molecular volume of greater than 250 cubic Å, alternately greater than 300 cubic Å, or alternately greater than 500 cubic Å.

Preferably $(Ar_3C)_d^+$ is $(Ph_3C)_d^+$, where Ph is a substituted or unsubstituted phenyl, preferably substituted with $C_1$ to $C_{40}$ hydrocarbyls or substituted $C_1$ to $C_{40}$ hydrocarbyls, preferably $C_1$ to $C_{20}$ alkyls or aromatics or substituted $C_1$ to $C_{20}$ alkyls or aromatics.

"Molecular volume" is used herein as an approximation of spatial steric bulk of an activator molecule in solution. Comparison of substituents with differing molecular volumes allows the substituent with the smaller molecular volume to be considered "less bulky" in comparison to the substituent with the larger molecular volume. Conversely, a substituent with a larger molecular volume may be considered "more bulky" than a substituent with a smaller molecular volume.

Molecular volume may be calculated as reported in "A Simple "Back of the Envelope" Method for Estimating the Densities and Molecular Volumes of Liquids and Solids," Journal of Chemical Education, Vol. 71, No. 11, November 1994, pp. 962-964. Molecular volume (MV), in units of cubic Å, is calculated using the formula: $MV=8.3V_s$, where $V_s$ is the scaled volume. $V_s$ is the sum of the relative volumes of the constituent atoms, and is calculated from the molecular formula of the substituent using the following table of relative volumes. For fused rings, the $V_s$ is decreased by 7.5% per fused ring.

| Element | Relative Volume |
|---|---|
| H | 1 |
| 1$^{st}$ short period, Li to F | 2 |
| 2$^{nd}$ short period, Na to Cl | 4 |
| 1$^{st}$ long period, K to Br | 5 |
| 2$^{nd}$ long period, Rb to I | 7.5 |
| 3$^{rd}$ long period, Cs to Bi | 9 |

For a list of particularly useful Bulky activators please see U.S. Ser. No. 61/494,730, filed Jun. 8, 2011, which is incorporated by reference herein.

In another embodiment, one or more of the NCAs is chosen from the activators described in U.S. Pat. No. 6,211,105.

Supports

The complexes described herein may be supported (with or without an activator) by any method effective to support other coordination catalyst systems, effective meaning that the catalyst so prepared can be used for oligomerizing or polymerizing olefin in a heterogeneous process. The catalyst precursor, activator, co-activator if needed, suitable solvent, and support may be added in any order or simultaneously. Typically, the complex and activator may be combined in solvent to form a solution. Then the support is added, and the mixture is stirred for 1 minute to 10 hours. The total solution volume may be greater than the pore volume of the support, but some embodiments limit the total solution volume below that needed to form a gel or slurry (about 90% to 400%, preferably about 100% to 200% of the pore volume). After stirring, the residual solvent is removed under vacuum, typically at ambient temperature and over 10-16 hours. But greater or lesser times and temperatures are possible.

The complex may also be supported absent the activator; in that case, the activator (and co-activator if needed) is added to a polymerization process's liquid phase. Additionally, two or more different complexes may be placed on the same support. Likewise, two or more activators or an activator and co-activator may be placed on the same support.

Suitable solid particle supports are typically comprised of polymeric or refractory oxide materials, each being preferably porous. Preferably, any support material that has an average particle size greater than 10 µm is suitable for use in this invention. Various embodiments select a porous support material, such as for example, talc, inorganic oxides, inorganic chlorides, for example magnesium chloride and resinous support materials such as polystyrene polyolefin or polymeric support compounds or any other organic support material and the like. Some embodiments select inorganic oxide materials as the support material including Group-2, -3, -4, -5, -13, or -14 metal or metalloid oxides. Some embodiments select the catalyst support materials to include silica, alumina, silica-alumina, and their mixtures. Other inorganic oxides may serve either alone or in combination with the silica, alumina, or silica-alumina. These are magnesia, titania, zirconia, and the like. Lewis acidic materials such as montmorillonite and similar clays may also serve as a support. In this case, the support can optionally double as the activator component; however, an additional activator may also be used.

The support material may be pretreated by any number of methods. For example, inorganic oxides may be calcined, chemically treated with dehydroxylating agents such as aluminum alkyls and the like, or both.

As stated above, polymeric carriers will also be suitable in accordance with the invention, see for example the descriptions in WO 95/15815 and U.S. Pat. No. 5,427,991. The methods disclosed may be used with the catalyst complexes, activators or catalyst systems of this invention to adsorb or absorb them on the polymeric supports, particularly if made up of porous particles, or may be chemically bound through functional groups bound to or in the polymer chains.

Useful supports typically have a surface area of from 10-700 m$^2$/g, a pore volume of 0.1-4.0 cc/g and an average particle size of 10-500 µm. Some embodiments select a surface area of 50-500 m$^2$/g, a pore volume of 0.5-3.5 cc/g, or an average particle size of 20-200 µm. Other embodiments select a surface area of 100-400 m$^2$/g, a pore volume of 0.8-3.0 cc/g, and an average particle size of 30-100 µm. Useful supports typically have a pore size of 10-1000 Angstroms, alternatively 50-500 Angstroms, or 75-350 Angstroms.

The catalyst complexes described herein are generally deposited on the support at a loading level of 10-100 micromoles of complex per gram of solid support; alternately 20-80 micromoles of complex per gram of solid support; or 40-60 micromoles of complex per gram of support. But greater or lesser values may be used provided that the total amount of solid complex does not exceed the support's pore volume.

Polymerization

Invention catalyst complexes are useful in polymerizing unsaturated monomers conventionally known to undergo metallocene-catalyzed polymerization such as solution, slurry, gas-phase, and high-pressure polymerization. Typically one or more of the complexes described herein, one or more activators, and one or more monomers are contacted to produce polymer. The complexes may be supported and as such will be particularly useful in the known, fixed-bed, moving-bed, fluid-bed, slurry, solution, or bulk operating modes conducted in single, series, or parallel reactors.

One or more reactors in series or in parallel may be used in the present invention. The complexes, activator and when required, co-activator, may be delivered as a solution or slurry, either separately to the reactor, activated in-line just prior to the reactor, or preactivated and pumped as an activated solution or slurry to the reactor. Polymerizations are carried out in either single reactor operation, in which monomer, comonomers, catalyst/activator/co-activator, optional scavenger, and optional modifiers are added continuously to a single reactor or in series reactor operation, in which the above components are added to each of two or more reactors connected in series. The catalyst components can be added to the first reactor in the series. The catalyst component may also be added to both reactors, with one component being added to first reaction and another component to other reactors. In one preferred embodiment, the complex is activated in the reactor in the presence of olefin.

In a particularly preferred embodiment, the polymerization process is a continuous process.

Polymerization process used herein typically comprises contacting one or more alkene monomers with the complexes (and, optionally, activator) described herein. For purpose of this invention alkenes are defined to include multi-alkenes (such as dialkenes) and alkenes having just one double bond. Polymerization may be homogeneous (solution or bulk polymerization) or heterogeneous (slurry—in a liquid diluent, or gas phase—in a gaseous diluent). In the case of heterogeneous slurry or gas phase polymerization, the complex and activator may be supported. Silica is useful as a support herein. Chain transfer agents (such as hydrogen or diethyl zinc) may be used in the practice of this invention.

The present polymerization processes may be conducted under conditions preferably including a temperature of about 30° C. to about 200° C., preferably from 60° C. to 195° C., preferably from 75° C. to 190° C. The process may be conducted at a pressure of from 0.05 to 1500 MPa. In a preferred embodiment, the pressure is between 1.7 MPa and 30 MPa, or in another embodiment, especially under supercritical conditions, the pressure is between 15 MPa and 1500 MPa.

Monomers

Monomers useful herein include olefins having from 2 to 40 carbon atoms, alternately 2 to 12 carbon atoms (preferably ethylene, propylene, butylene, pentene, hexene, heptene, octene, nonene, decene, and dodecene) and optionally also polyenes (such as dienes). Particularly preferred monomers include ethylene, and mixtures of $C_2$ to $C_{10}$ alpha olefins, such as ethylene-propylene, ethylene-hexene, ethylene-octene, propylene-hexene, and the like.

The complexes described herein are also particularly effective for the polymerization of ethylene, either alone or in combination with at least one other olefinically unsaturated monomer, such as a $C_3$ to $C_{20}$ α-olefin, and particularly a $C_3$ to $C_{12}$ α-olefin. Likewise, the present complexes are also particularly effective for the polymerization of propylene, either alone or in combination with at least one other olefinically unsaturated monomer, such as ethylene or a $C_4$ to $C_{20}$ α-olefin, and particularly a $C_4$ to $C_{20}$ α-olefin. Examples of preferred α-olefins include ethylene, propylene, butene-1, pentene-1, hexene-1, heptene-1, octene-1, nonene-1, decene-1, dodecene-1, 4-methylpentene-1, 3-methylpentene-1, 3, 5, 5-trimethylhexene-1, and 5-ethylnonene-1.

In some embodiments, the monomer mixture may also comprise one or more dienes at up to 10 wt %, such as from 0.00001 to 1.0 wt %, for example from 0.002 to 0.5 wt %, such as from 0.003 to 0.2 wt %, based upon the monomer mixture. Non-limiting examples of useful dienes include, cyclopentadiene, norbornadiene, dicyclopentadiene, 5-ethylidene-2-norbornene, 5-vinyl-2-norbornene, 1,4-hexadiene, 1,5-hexadiene, 1,5-heptadiene, 1,6-heptadiene, 6-methyl-1,6-heptadiene, 1,7-octadiene, 7-methyl-1,7-octadiene, 1,9-decadiene, and 9-methyl-1,9-decadiene.

Where olefins are used that give rise to short chain branching, such as propylene, the catalyst systems may, under appropriate conditions, generate stereoregular polymers or polymers having stereoregular sequences in the polymer chains.

In a preferred embodiment, the catalyst complexes described herein, preferably as represented by formula (I) or (II), are used in any polymerization process described above to produce ethylene homopolymers or copolymers, propylene homopolymers or copolymers. In a preferred embodiment, the catalyst complexes described herein, preferably as represented by formula (I) or (II), are used in any polymerization process described above to produce polyalphaolefins (PAO's), e.g., polymers of $C_3$ to $C_{40}$ alphaolefins, having low number average molecular weight (e.g., 30,000 g/mol or less (as determined as described in U.S. 2008/0045638, pg 36-38), such as dimers, trimers, tetramers, pentamers) of $C_4$ to $C_{24}$ (preferably $C_5$ to $C_{18}$, preferably $C_6$ to $C_{14}$, even preferably $C_8$ to $C_{12}$, most preferably $C_{10}$) branched or linear alpha-olefins, provided that $C_3$ and $C_4$ alpha-olefins are present at 10 wt % or less. Suitable olefins include propylene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, and blends thereof. Polymers of linear alpha olefins (LAO's) with only even carbon numbers between 6 and 18 (inclusive) are particularly preferred. In one embodiment, a single LAO is used to prepare the oligomers. In this case, a preferred embodiment involves the oligomerization of 1-decene, and the PAO is a mixture of oligomers (including, for example, dimers, trimers, tetramers, pentamers, and higher) of 1-decene. In another embodiment, the PAO comprises oligomers of two or more $C_3$ to $C_{18}$ LAOs (preferably $C_5$ to $C_{18}$ LAOs), to make 'bipolymer' or 'terpolymer' or higher-order copolymer combinations, provided that $C_3$ and $C_4$ LAOs are present at 10 wt % or less. In this case, a preferred embodiment involves the polymerization of a mixture of 1-octene, 1-decene, and 1-dodecene, and the PAO is a mixture of oligomers (for example, dimers, trimers, tetramers, pentamers, and higher) of 1-octene, 1-decene, and 1-dodecene. In a preferred embodiment, the PAO has a viscosity index (ASTM D 2270) of 120 or more, preferably 150 or more, preferably 200 or more and a pour point (ASTM D 97) of −20° C. or less, preferably −25° C. or less, preferably −30° C. or less and a flash point (ASM D 92) of 200° C. or more, preferably 220° C. or more, preferably 250° C. or more.

Scavengers

In some embodiments, when using the complexes described herein, particularly when they are immobilized on a support, the catalyst system will additionally comprise one or more scavenging compounds. Here, the term scavenging compound means a compound that removes polar impurities from the reaction environment. These impurities adversely affect catalyst activity and stability. Typically, the scavenging compound will be an organometallic compound such as the Group-13 organometallic compounds of U.S. Pat. Nos. 5,153,157, 5,241,025 and WO-A-91/09882, WO-A-94/03506, WO-A-93/14132, and that of WO 95/07941. Exemplary compounds include triethyl aluminum, triethyl borane, tri-iso-butyl aluminum, methyl alumoxane, iso-butyl alumoxane, and tri-n-octyl aluminum. Those scavenging compounds having bulky or $C_6$-$C_{20}$ linear hydrocarbyl substituents connected to the metal or metalloid center usually minimize adverse interaction with the active catalyst. Examples include triethylaluminum, but more preferably, bulky compounds such as tri-iso-butyl aluminum, tri-iso-prenyl aluminum, and long-chain linear alkyl-substituted aluminum compounds, such as tri-n-hexyl aluminum, tri-n-octyl aluminum, or tri-n-dodecyl aluminum. When alumoxane is used as the activator, any excess over that needed for activation will scavenge impurities and additional scavenging compounds may be unnecessary. Alumoxanes also may be added in scavenging quantities with other activators, e.g., methylalumoxane, $[Me_2HNPh]^+[B(pfp)_4]^-$ or $B(pfp)_3$ (perfluorophenyl=pfp=$C_6F_5$).

In a preferred embodiment, two or more complexes are combined with diethyl zinc in the same reactor with monomer. Alternately, one or more complexes are combined with another catalyst (such as a metallocene) and diethyl zinc in the same reactor with monomer.

Polymer Products

While the molecular weight of the polymers produced herein is influenced by reactor conditions including temperature, monomer concentration and pressure, the presence of chain terminating agents and the like, the homopolymer and copolymer products produced by the present process may have an Mw of about 1,000 to about 2,000,000 g/mol, alternately of about 30,000 to about 600,000 g/mol, or alternately of about 100,000 to about 500,000 g/mol, as determined by Gel Permeation Chromatography. Preferred polymers produced here may be homopolymers or copolymers. In a preferred embodiment, the comonomer(s) are present at up to 50 mol %, preferably from 0.01 to 40 mol %, preferably 1 to 30 mol %, preferably from 5 to 20 mol %.

End Uses

Articles made using polymers produced herein may include, for example, molded articles (such as containers and bottles, e.g., household containers, industrial chemical containers, personal care bottles, medical containers, fuel tanks, and storageware, toys, sheets, pipes, tubing) films, non-wovens, and the like. It should be appreciated that the list of applications above is merely exemplary, and is not intended to be limiting.

In another embodiment, this invention relates to:
1. A pyridyldiamido transition metal complex for use in alkene polymerization represented by the formula: (I) or (II):

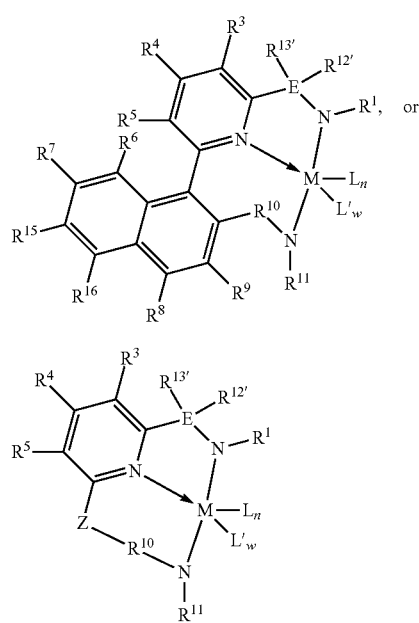

wherein:

M is a Group 3, 4, 5, 6, 7, 8, 9, 10, 11, or 12 metal (preferably a Group 4 metal, preferably Ti, Zr or Hf);

$R^1$ is selected from the group consisting of hydrocarbyls, substituted hydrocarbyls, and silyl groups (preferably alkyl, aryl, heteroaryl, and silyl groups);

$R^{11}$ is selected from the group consisting of substituted 5 or 6 (preferably 6) membered aromatic rings, (such as substituted 5 or 6 membered rings where the ring atoms are carbon or heterocyclic rings having 1, 2 or 3 heteroatoms in the ring (such as N, O or S)) where the substitution is a hydrocarbyl group, a heteroatom, or a heteroatom containing group, preferably $R^{11}$ is a substituted aryl group, preferably a 2,6 or 2,4,6 substituted aryl group;

$R^{10}$ is -E*$(R^{12})(R^{13})$— (preferably $R^{12}$ and $R^{13}$ are the same, preferably $R^{10}$ is $CH_2$;

E and E* are independently carbon, silicon, or germanium (preferably carbon);

each $R^{12}$ and $R^{13}$ are independently selected from the group consisting of hydrogen, hydrocarbyl, and substituted hydrocarbyl, alkoxy, silyl, amino, aryloxy, halogen, and phosphino (preferably hydrogen, alkyl, aryl, alkoxy, silyl, amino, aryloxy, heteroaryl, halogen, and phosphino), $R^{12}$ and $R^{13}$ may be joined to form a saturated, substituted or unsubstituted hydrocarbyl ring, where the ring has 4, 5, 6, or 7 ring carbon atoms and where substitutions on the ring can join to form additional rings, or $R^{12}$ and $R^{13}$ may be joined to form a saturated heterocyclic ring, or a saturated substituted heterocyclic ring where substitutions on the ring can join to form additional rings;

each $R^{12}$* and $R^{13}$* is independently selected from the group consisting of hydrogen, C1 to C5 hydrocarbyls, substituted C1 to C5 hydrocarbyls, preferably hydrogen, methyl, ethyl, propyl, butyl, pentyl;

$R^3$, $R^4$, and $R^5$ are independently selected from the group consisting of hydrogen, hydrocarbyls, substituted hydrocarbyls, alkoxy, aryloxy, halogen, amino, and silyl, (preferably hydrogen, alkyl, alkoxy, aryloxy, halogen, amino, silyl, and aryl), and wherein adjacent R groups ($R^3$ & $R^4$ and/or $R^4$ & $R^5$) may be joined to form a substituted or unsubstituted hydrocarbyl or heterocyclic ring, where the ring has 5, 6, 7, or 8 ring atoms and where substitutions on the ring can join to form additional rings;

$R^6$, $R^7$, $R^8$, $R^9$, $R^{15}$, and $R^{16}$ are independently selected from the group consisting of hydrogen, hydrocarbyls, substituted hydrocarbyls, alkoxy, halogen, amino, and silyl, and the pairs of positions, and wherein adjacent R groups ($R^6$ & $R^7$, and/or $R^7$ & $R^{15}$, and/or $R^{16}$ & $R^{15}$, and/or $R^8$ & $R^9$) may be joined to form a saturated, substituted or unsubstituted hydrocarbyl or heterocyclic ring, where the ring has 5, 6, 7, or 8 ring carbon atoms and where substitutions on the ring can join to form additional rings;

L is an anionic leaving group, where the L groups may be the same or different and any two L groups may be linked to form a dianionic leaving group;

n is 0, 1, 2, 3, or 4;

L' is neutral Lewis base;

w is 0, 1, 2, 3, or 4;

Z is —$(R^{14}*)_pQ-J(R^{15}*)_q$— where Q or J is bonded to $R^{10}$;

J is C or Si, preferably C;

Q is C, O, N, or Si, preferably C;

$R^{14}$* and $R^{15}$* are independently selected from the group consisting of hydrogen, hydrocarbyls, and substituted hydrocarbyls, (preferably hydrogen and alkyls), and wherein adjacent $R^{14}$* and $R^{15}$* groups may be joined to form an aromatic or saturated, substituted or unsubstituted hydrocarbyl ring, where the ring has 5, 6, 7, or 8 ring carbon atoms and where substitutions on the ring can join to form additional rings;

p is 1 or 2; and q is 1 or 2.

2. A complex according to paragraph 1 in which M is Ti, Zr, or Hf.

3. A complex according to paragraph 1 or 2 in which $R^{10}$ is $CH_2$.

4. A complex according to any of the preceding paragraphs 1 to 3 in which $R^1$ and $R^3$ to $R^9$ and/or $R^{12}$ to $R^{13}$ above, including $R^{14*}$, $R^{15*}$, $R^{12*}$, and $R^{13*}$, contain no more than 30 carbon atoms, preferably from 2 to 20 carbon atoms.
5. A complex according to any of the preceding paragraphs 1 to 4 in which E is carbon and $R_1$ is selected from phenyl groups that are variously substituted with between zero to five substituents that include F, Cl, Br, I, $CF_3$, $NO_2$, alkoxy, dialkylamino, hydrocarbyl (such as alkyl and aryl), and substituted hydrocarbyls (such as heteroaryl), groups with from one to ten carbons.
6. A complex according to any of the preceding paragraphs 1 to 5 in which each L is, independently, selected from halide, alkyl, aryl, alkoxy, amido, hydrido, phenoxy, hydroxy, silyl, allyl, alkenyl, triflate, alkylsulfonate, arylsulfonate, and alkynyl; and/or L' is, independently, selected from ethers, thio-ethers, amines, nitriles, imines, pyridines, and phosphines.
7. A complex according to any of the preceding paragraphs 1 to 6 in which one of $R^{12*}$ and $R^{13*}$ is preferably hydrogen.
8. A complex according to any of the preceding paragraphs 1 to 7 in which $R^{12*}$ and $R^{13*}$ are the same.
9. A complex according to any of the preceding paragraphs 1 to 8 wherein $R^{11}$ is selected from aryl groups that are variously substituted with between zero to five substituents that include F, Cl, Br, I, $CF_3$, $NO_2$, alkoxy, dialkylamino, aryl, and alkyl groups with between one to ten carbons, preferably $R^{11}$ is 2,6 or 2,4,6 substituted aryl, preferably where the substituents are methyl, ethyl, methoxy, propyl, tert-butyl, butyl, isopropyl, pentyl, hexyl, isobutyl, chloro, fluoro, bromo, iodo, trimethylsilyl, or triethylsilyl. In a preferred embodiment, $R^{11}$ is 2,4,6-trimethylphenyl, 2,6-dimethylphenyl, 2,6-diethylphenyl, 2,6-diisobutylphenyl, 2,5-dimethylphenyl, 2,4,5-trimethylphenyl, 2,3,4,5,6-pentamethylphenyl, 2,6-diisopropylphenyl, or 2,4,6-triisopropylphenyl.
10. A catalyst system comprising a complex according to any of paragraphs 1 to 9 and an activator or cocatalyst such as alumoxane or a non-coordinating anion.
11. A polymerization process comprising contacting alkene monomer with a complex according to any of paragraphs 1 to 9 or the catalyst system of paragraph 10.

EXAMPLES

Sources of Chemicals. Unless stated otherwise the chemicals used in the syntheses described below were purchased from commercial suppliers. 6-Bromopyridine-2-carboxaldehyde (Acros), 1-bromo-2-methylnaphthalene (Aldrich), 2-isopropoxy-4,4,5,5-tetramethyl-1,3,2-dioxaborolane (Aldrich), tert-butylamine (Merck), 2,4,6-trimethylaniline (Acros), 2,6-diisopropylaniline (Acros), 2-methylaniline (Acros), 2.5 M nBuLi in hexanes (Acros), tert-butyl phenylcarbamate (Acros), $NaBH_3CN$ (Aldrich), 1,2-dibromoethane (Acros), N-bromosuccinimide (Acros), $Pd(PPh_3)_4$ (Aldrich), triethylamine (Acros), ether (Merck), THF (Merck), ethyl acetate (Merck), carbon tetrachloride (Merck), DMF, dimethylformamide, (Merck), methanol (Merck), toluene (Merck), hexanes (Merck), dichloromethane (Merck), dry ethanol (Merck), magnesium turnings (Acros), $MgSO_4$ (Merck), molecular sieves 4 angstrom (Merck), $Na_2CO_3(H_2O)_{10}$ (Merck), $K_2CO_3$ (Merck), 12 M hydrochloric acid (Merck), 88% formic acid (Merck) and $CDCl_3$ (Deutero GmbH), 2-(bromomethyl)phenyl boronic acid pinacol ester (Aldrich) were used as received. Additionally, 1.6 M PhLi in ether was obtained from phenyl bromide (Acros) and magnesium turnings in ether. DMF (Merck) was dried and distilled over $CaH_2$. Diethyl ether and THF freshly distilled from benzophenone ketyl were used for organometallic synthesis and catalysis. $Zr(NMe_2)_2Cl_2(dme)$ (dme=1,2-dimethoxyethane) and $Hf(NMe_2)_2Cl_2(dme)$ were prepared as described by Erker and coworkers in Organometallics 2000, 19, 127-134. $ZrBn_2Cl_2(Et_2O)_n$ (n=1-2) was prepared by reaction of one equivalent of $ZrBn_4$ (Strem) with $ZrCl_4$ (Strem) in $Et_2O$ for 5 hours followed by filtration and crystallization of the product. $HfBn_2Cl_2(Et_2O)_n$ (n=1-2) was prepared by reaction of one equivalent of $HfBn_4$ (Strem) with $ZrCl_4$ (Strem) in $Et_2O$ for 5 hours followed by filtration and crystallization of the product.

Synthesis of Pyridyl Diamines

Outlined in Schemes 1 is the general synthetic routes that was used to prepare pyridyl diamines. In the Scheme pin is pinacolate (2,3 dimethyl butane 2,3 diolate), Me is methyl, Mes is mesityl, Boc is t-butylcarbonate, Ph is phenyl, Dipp is 2,6-diisopropylphenyl, 2-iPrPh is 2-isopropylphenyl.

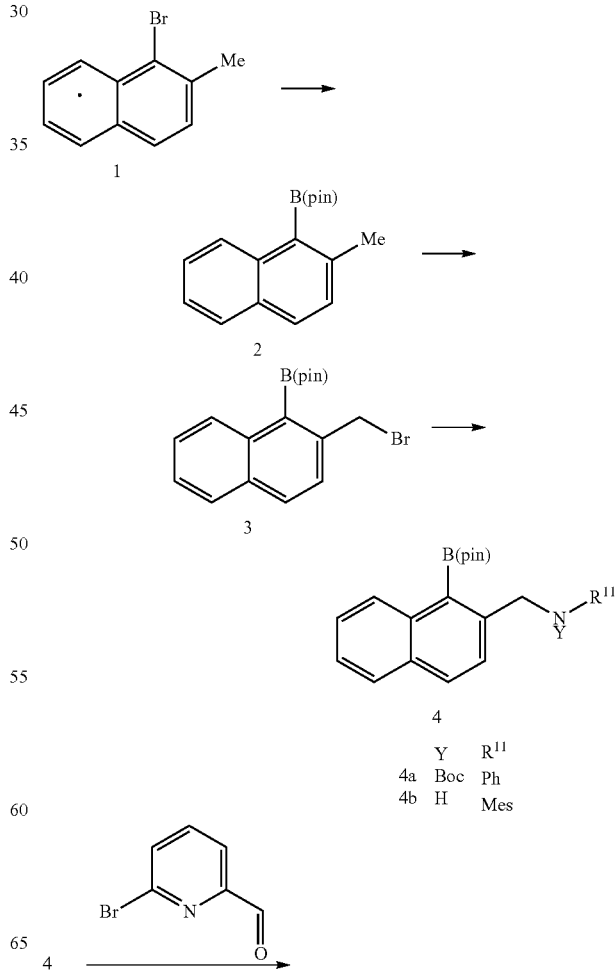

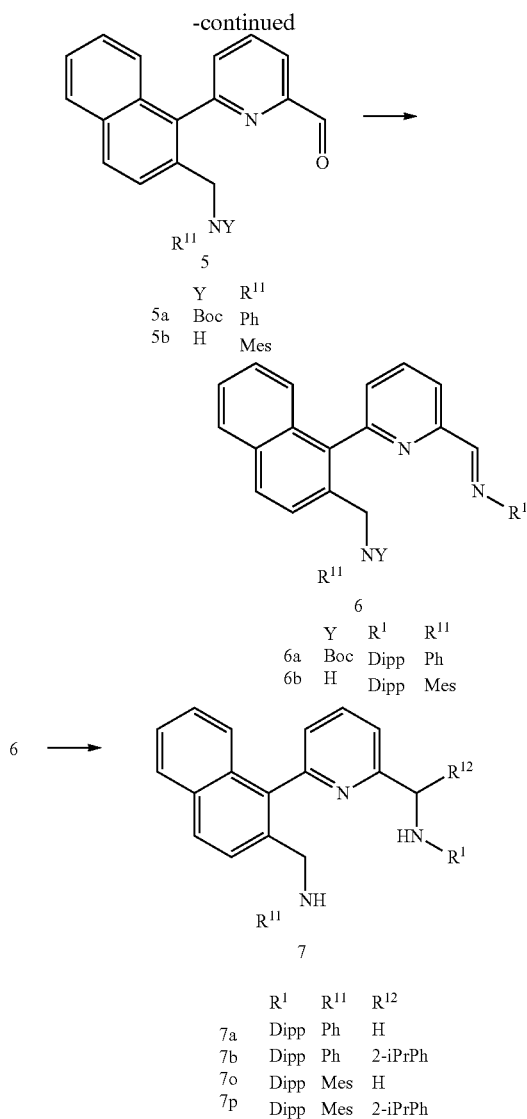

| | Y | R¹¹ |
|---|---|---|
| 5a | Boc | Ph |
| 5b | H | Mes |

| | Y | R¹ | R¹¹ |
|---|---|---|---|
| 6a | Boc | Dipp | Ph |
| 6b | H | Dipp | Mes |

| | R¹ | R¹¹ | R¹² |
|---|---|---|---|
| 7a | Dipp | Ph | H |
| 7b | Dipp | Ph | 2-iPrPh |
| 7o | Dipp | Mes | H |
| 7p | Dipp | Mes | 2-iPrPh |

4,4,5,5-Tetramethyl-2-(2-methyl-1-naphthyl)-1,3,2-dioxaborolane (2). 1,2-Dibromoethane (~0.3 ml) was added to 6.10 g (250 mmol) magnesium turnings in 1000 cm³ of THF. This mixture was stirred for 10 min, and then 55.3 g (250 mmol) of 1-bromo-2-methylnaphthalene was added for 1 h by vigorous stirring at room temperature for 3.5 h. Thereafter, 46.5 g (250 mmol) of 2-isopropoxy-4,4,5,5-tetramethyl-1,3,2-dioxaborolane was added in one portion. The resulting mixture was stirred for 15 minutes and then was poured into 1000 cm³ of cold water. The product was extracted with 3×300 ml of ethyl acetate. The organic layer was separated, washed by water, brine, then dried over MgSO₄, and, finally; evaporated to dryness. The resulting white solid was washed by 2×75 ml of pentane and dried in vacuum. Yield 47.3 g (70%). Anal. calc. for $C_{17}H_{21}BO_2$: C, 76.14; H, 7.89. Found: C, 76.31; H, 8.02. ¹H NMR (CDCl₃): 8.12 (m, 1H, 8-H), 7.77 (m, 1H, 5-H), 7.75 (d, J=8.4 Hz, 1H, 4-H), 7.44 (m, 1H, 7-H), 7.38 (m, 1H, 6-H), 7.28 (d, J=8.4 Hz, 1H, 3-H), 2.63 (s, 3H, 2-Me), 1.48 (s, 12H, CMe₂CMe₂).

2-[2-(Bromomethyl)-1-naphthyl]-4,4,5,5-tetramethyl-1,3,2-dioxaborolane (3). A mixture of 47.3 g (176 mmol) of 4,4,5,5-tetramethyl-2-(2-methyl-1-naphthyl)-1,3,2-dioxaborolane, 33.0 g (185 mmol) of NBS (N-Bromosuccinimide) and 0.17 g of benzoyl peroxide in 340 ml of CCl₄ was stirred at 75° C. for 14 h. Thereafter the reaction mixture was cooled to room temperature, filtered through glass frit (G3), and the filtrate was evaporated to dryness. This procedure gave 62.2 g (99%) of beige solid. Anal. calc. for $C_{17}H_{20}BBrO_2$: C, 58.83; H, 5.81. Found: C, 59.00; H, 5.95. ¹H NMR (CDCl₃): 8.30 (m, 1H, 8-H), 7.84 (d, J=8.3 Hz, 1H, 4-H), 7.79 (m, 1H, 5-H), 7.43-7.52 (m, 3H, 3,6,7-H), 4.96 (s, 2H, CH₂Br), 1.51 (s, 12H, CMe₂CMe₂).

tert-Butyl phenyl{[1-(4,4,5,5-tetramethyl-1,3,2-dioxaborolan-2-yl)-2-naphthyl]methyl}carbamate (4a). To a suspension of 17.0 g (88.1 mmol) of tert-butyl phenylcarbamate in 150 ml of hexanes 35.2 ml (88.1 mmol) of 2.5 M nBuLi in hexanes was slowly added at gentle reflux for ca. 15 min. This mixture was stirred for additional 30 minutes and then evaporated to dryness. The resulting white powder was added to a solution of 30.6 g (88.1 mmol) of 2-[2-(bromomethyl)-1-naphthyl]-4,4,5,5-tetramethyl-1,3,2-dioxaborolane in 300 ml of DMF. This mixture was stirred for 20 minutes at 75° C. and then poured into 1200 cm³ of cold water. The product was extracted with 3×200 ml of ethyl acetate. The combined organic extract was washed by 2×300 ml of water, dried over MgSO₄, and then evaporated to dryness. The crude product was purified by flash chromatography on silica gel 60 (40-63 um, eluent: hexanes-ethyl acetate=20:1, vol. then 10:1, vol.). Yield 28.0 g (69%) of yellowish oil. Anal. calc. for $C_{28}H_{34}BNO_4$: C, 73.21; H, 7.46; N, 3.05. Found: C, 73.12; H, 7.62; N, 3.24. ¹H NMR (CDCl₃): 8.19 (m, 1H, 8-H in naphthyl), 7.85 (d, J=8.6 Hz, 1H, 4-H in naphthyl), 7.77 (m, 1H, 5-H in naphthyl), 7.60 (d, J=8.6 Hz, 1H, 3-H in naphthyl), 7.45 (m, 1H, 7-H in naphthyl), 7.40 (m, 1H, 6-H in naphthyl), 7.20 (m, 2H, 3,5-H in Ph), 7.13 (m,\2H, 2,6-H in Ph), 7.08 (m, 1H, 4-H in Ph), 5.21 (s, 2H, CH₂N), 1.42 (s, 9H, ᵗBu), 1.38 (s, 12H, CMe₂CMe₂).

2,4,6-Trimethyl-N-{[1-(4,4,5,5-tetramethyl-1,3,2-dioxaborolan-2-yl)-2-naphthyl]methyl}aniline (4b). A mixture of 29.2 g (216 mmol) of 2,4,6-trimethylaniline, 50.0 g (144 mmol) of 2-[2-(bromomethyl)-1-naphthyl]-4,4,5,5-tetramethyl-1,3,2-dioxaborolane, and 22.0 g (159 mmol) of K₂CO₃ in 1100 cm³ of DMF was stirred at 80° C. for 12 h. The resulting mixture was poured into 2000 cm³ of water. The product was extracted with 3×400 ml of ethyl acetate. The combined extract was dried over MgSO₄ and then evaporated to dryness. The product was isolated by flash chromatography on silica gel 60 (40-63 um; eluent: dichloromethane). Yield 45.0 g (78%). Anal. Calc. For $C_{26}H_{32}BNO_2$: C, 77.81; H, 8.04; N, 3.49. Found: C, 77.99; H, 8.24; N, 3.26. ¹H NMR (CDCl₃): 8.27 (m, 1H, 8-H in naphthyl), 7.84 (m, 1H, 5-H in naphthyl), 7.81 (d, J=8.4 Hz, 1H, 4-H in naphthyl), 7.54 (m, 1H, 7-H in naphthyl), 7.48 (m, 1H, 6-H in naphthyl), 7.37 (d, J=8:4 Hz, 1H, 3-H in naphthyl), 6.87 (s, 2H, 3,5-H in mesityl), 4.39 (s, 2H, CH₂N), 3.68 (br.s, 1H, NH), 2.31 (s, 6H, 2,6-Me in mesityl), 2.30 (s, 3H, 4-H in mesityl), 1.49 (s, 12H, CMe₂CMe₂).

tert-Butyl {[1-(6-formylpyridin-2-yl)-2-naphthyl]methyl}phenylcarbamate (5a). A solution of 24.3 g (84.8 mmol) of Na₂CO₃(H₂O)₁₀ in a mixture of 120 ml of methanol and 450 ml of water was added to a mixture of 6.30 g (33.9 mmol) of 6-bromopyridine-2-carbaldehyde, 15.6 g (33.9 mmol) of tert-butyl phenyl{[1-(4,4,5,5-tetramethyl-1,3,2-dioxaborolan-2-yl)-2-naphthyl]methyl}carbamate and 1.96 g (1.70 mmol) of Pd(PPh₃)₄ in 600 ml of toluene by vigorous stirring at room temperature. The resulting mixture was stirred at 80° C. for 12 h. Thereafter, this mixture was cooled to room temperature, the organic layer was separated, dried over MgSO₄, and then evaporated to dryness. The product was isolated by flash chromatography on silica gel 60 (40-63 um; eluent: hexanes-ethyl acetate=50:1 and then 10:1, vol.). Yield 9.50 g (64%). Anal. calc. for $C_{28}H_{26}N_2O_3$: C, 76.69; H, 5.98; N, 6.39. Found: C, 76.87; H, 6.12; N, 6.25. $^1$H NMR (CDCl$_3$): 10.03 (s, 1H, CHO), 7.94-7.98 (m, 2H, 3,5-H in Py), 7.88 (m, 1H, 8-H in naphthyl), 7.83 (m, 1H, 4-H in Py), 7.75 (d, J=8.6 Hz, 1H, 4-H in naphthyl), 7.45 (m, 1H, 7-H in naphthyl), 7.34 (m, 1H, 6-H in naphthyl), 7.11-7.18 (m, 4H, 5-H in naphthyl and 3,4,5-H in Ph), 7.03 (d, J=8.6 Hz, 1H, 3-H in naphthyl), 6.93 (m, 2H, 2,6-H in Ph), 5.06 (d, J=15.9 Hz, 1H, CHH'N), 4.52 (d, J=15.9 Hz, 1H, CHH'N), 1.40 (s, 9H, $^t$Bu).

6-{2-[(Mesitylamino)methyl]-1-naphthyl}pyridine-2-carbaldehyde (5b). A solution of 32.4 g (113 mmol) of Na$_2$CO$_3$ (H$_2$O)$_{10}$ in a mixture of 180 ml of methanol and 600 ml of water was added to a mixture of 8.37 g (45.0 mmol) of 6-bromopyridine-2-carbaldehyde, 18.1 g (45.0 mmol) of 2,4,6-trimethyl-N-{[1-(4,4,5,5-tetramethyl-1,3,2-dioxaborolan-2-yl)-2-naphthyl]methyl}aniline and 2.65 g (2.30 mmol) of Pd(PPh$_3$)$_4$ in 600 ml of toluene by vigorous stirring at room temperature. The resulting mixture was stirred at 80° C. for 12 h. Thereafter, this mixture was cooled to room temperature, the organic layer was separated, dried over MgSO$_4$, and then evaporated to dryness. The product was isolated by flash chromatography on silica gel 60 (40-63 um; eluent: dichloromethane-ethyl acetate=100:1 and then 10:1, vol.). Yield 10.7 g (63%). Anal. calc. for $C_{26}H_{24}N_2O$: C, 82.07; H, 6.36; N, 7.36. Found: C, 82.24; H, 6.49; N, 7.18. $^1$H NMR (CDCl$_3$): 10.12 (s, 1H, CHO), 8.06 (m, 1H, 3-H in Py), 7.90-7.99 (m, 3H, 5,7,8-H in naphthyl), 7.63 (d, J=8.3 Hz, 4-H in naphthyl), 7.54 (m, 1H, 5-H in Py), 7.49 (m, 1H, 4-H in Py), 7.39 (m, 1H, 6-H in naphthyl), 7.28 (d, J=8.3 Hz, 3-H in naphthyl), 6.74 (s, 2H, 3,5-H in mesityl), 3.98 (d, J=13.1 Hz, 1H, CHH'N), 3.89 (d, J=13.1 Hz, 1H, CHH'N), 3.37 (br.s, 1H, NH), 2.20 (s, 3H, 4-Me in mesityl), 2.04 (s, 6H, 2,6-Me in mesityl).

N-((1-(6-((2,6-Diisopropylphenylimino)methyl)pyridin-2-yl)naphthalen-2-yl)methyl)-2,4,6-trimethylaniline (6b). Benzene (200 mL) was added to compound 5b (6.69 g, 17.6 mmol), and 2,6-diisopropylaniline (3.12 g, 17.6 mmol), and p-toluenesulfonic acid monohydrate (5 mg) in a 500 mL round-bottomed flask fitted with a Dean-Stark trap. The mixture was heated to reflux under nitrogen. After 2 hours, $^1$H NMR spectroscopy of an aliquot indicated that the reaction had proceeded to around 90% completion. All but about 50 mL of the benzene was removed by distillation and toluene (200 mL) was added. The mixture was heated to reflux and most of the toluene was removed by distillation. Drying of the residue under reduced pressure afforded a dirty yellow solid. Dissolution of the solid in warm Et2O, followed by filtration and cooling to −20° C. afforded 6b as nice yellow crystals. Yield from two crops: 6.5 g, 69%. $^1$H NMR (500 MHz, CD$_2$Cl$_2$): 8.36 (d, 1H), 8.33 (s, 1H), 7.97 (t, 1H), 7.93 (d, 2H), 7.59 (d, 1H), 7.39-7.51 (m, 4H), 7.17 (d, 2H), 7.10 (m, 1H), 6.72 (s, 2H), 4.01 (br d, 1H), 3.92 (d, 1H), 3.39 (br, 1H), 3.03 (sept, 2H), 2.18 (s, 3H), 2.03 (s, 6H), 1.18 (d, 12H).

2,6-Diisopropyl-N-((6-(2-((phenylamino)methyl)naphthalen-1-yl)pyridin-2-yl)methyl)aniline (7a). Compound 5a (1.95 g, 4.43 mmol) and tetrahydrofuran (30 mL) were combined to form a solution. Then 2,6-diisopropylaniline (0.785 g, 4.43 mmol) and 4 angstrom molecular sieves (ca. 20 mL) were added followed by a catalytic amount of p-toluenesulfonic acid monohydrate (0.005 g, 0.03 mmol). The mixture became yellow immediately. After stirring overnight the mixture was filtered and evaporated to afford the imine 6a as an oil. This was then dissolved in methanol (30 mL) and NaBH$_3$CN (0.45 g) was added followed by a few drops of 85% formic acid. The mixture was heated to reflux. Additional NaBH$_3$CN (0.45 g) and a couple drops of the formic acid were added after 15 minutes. After another 15 minutes a third portion of NaBH$_3$CN (0.45 g) and a couple drops of the formic acid were added. After a total of 2.5 hours at reflux the pale yellow mixture was poured into water (250 mL) and extracted with Et$_2$O (150 mL). The organics were dried with brine then evaporated to an oil with some water or methanol separating out. This was extracted with Et$_2$O (20 mL), dried over magnesium sulfate, filtered, and evaporated to a residue containing the Boc-protected amine product. This was dissolved chloroform (40 mL) and trifluoroacetic acid (16 mL) was added. The mixture was heated to 55° C. for 1 hour, during which time gas evolved. The mixture was then poured into 3 M NaOH (125 mL) and stirred for several minutes. The organics were extracted into Et$_2$O (200 mL) then separated, dried over sodium sulfate, and evaporated to a slightly colored oil. The crude product was purified by chromatography on basic alumina using 5:1 hexanes:CH$_2$Cl$_2$ with an increasing gradient of ethyl acetate (0.5% to 10%). The product was isolated as a thick, purple-tinted oil. $^1$H NMR (500 MHz, CD$_2$Cl$_2$): 7.93 (t, 2H), 7.85 (t, 1H), 7.69 (d, 1H), 7.37-7.52 (m, 5H), 7.00-7.11 (m, 5H), 6.63 (t, 1H), 6.57 (d, 2H), 4.06-4.37 (m, 6H), 3.33 (sept, 2H), 1.16 (d, 12H).

2,6-Diisopropyl-N-((2-isopropylphenyl)(6-(2-((phenylamino)methyl)naphthalen-1-yl)pyridin-2-yl)methyl)aniline (7b). Compound 5a (2.28 g, 5.18 mmol), tetrahydrofuran (50 mL), and 4 angstrom molecular sieves (ca. 20 mL) were combined. Then 2,6-diisopropylaniline (0.918 g, 5.18 mmol) and a catalytic amount of p-toluenesulfonic acid monohydrate (0.005 g, 0.03 mmol) were added. The mixture was heated to 45° C. for 14 hours. Then the mixture was filtered and fresh molecular sieves (ca. 15 mL) were added followed by additional p-toluenesulfonic acid monohydrate (0.005 g, 0.03 mmol). After heating at 50° C. for 2 hours the mixture was filtered and evaporated to a residue of the imine 6a. Then Et$_2$O (30 mL) was added, and the resulting solution was cooled to −80° C. An Et$_2$O (5 mL) solution of 2-isopropylphenyllithium (0.653 g, 5.18 mmol) was added dropwise. The mixture was then allowed to slowly warm to ambient temperature over a couple of hours. Then the mixture was poured into water (100 mL) and the organics were separated, dried over brine then magnesium sulfate, filtered, and evaporated to a residue. The residue was dissolved in chloroform (25 mL), and trifluoroacetic acid (10 mL) was added. The mixture was heated to reflux for 40 minutes, during which time gas evolved. The mixture was cooled to ambient temperature and 3 M NaOH (60 mL) was added. After stirring for several minutes, the organics were separated, dried over brine then magnesium sulfate, filtered through diatomaceous earth, and evaporated to yield the crude product. This was purified by chromatography on basic alumina using 5:1 hexanes: CH$_2$Cl$_2$ with an increasing gradient of ethyl acetate (1% to 10%). The product was isolated as a foam-like solid. The $^1$H NMR spectrum of 7b in CD$_2$Cl$_2$ is complex due to the presence of more than one diastereoisomer.

N-((1-(6-((2,6-Diisopropylphenylamino)methyl)pyridin-2-yl)naphthalen-2-yl)methyl)-2,4,6-trimethylaniline (7o). Methanol (30 mL), toluene (10 mL), and compound 6b (2.11 g, 3.91 mmol) were heated to reflux under nitrogen. Formic acid (95%) (5 drops) was added followed by portions of NaBH$_3$CN (0.983 g, 15.6 mmol). The borohydride was added in four portions over an hour. After 3 hours at reflux the yellow color of the imine had faded completely and the volatiles were removed by evaporation on a rotary evaporator. Water (20 mL) and Et$_2$O (30 mL) were added, and the organics were separated and dried over brine. The ether solution was then dried over MgSO$_4$, filtered, and evaporated to give the diamine 7o as a pale pink solid. Yield: 2.1 g, 99%. $^1$H NMR (500 MHz, CD$_2$-Cl$_2$): 7.90 (t, 2H), 7.82 (t, 1H), 7.56 (d, 1H), 7.38-7.52 (m, 4H), 7.29 (d, 1H), 7.07 (d, 2H), 7.03 (m, 1H), 6.74 (s, 2H), 4.28 (m, 2H), 4.08 (br t, 1H), 3.96 (br, 2H), 3.45 (m, 1H), 3.33 sept, 2H), 2.19 (s, 3H), 2.05 (s, 6H), 1.15 (d, 12H).

N-((1-(6-((2,6-Diisopropylphenylamino)(2-isopropylphenyl)methyl)pyridin-2-yl)naphthalen-2-yl)methyl)-2,4,6-trimethylaniline (7p). Et$_2$O (40 mL) was added to compound 6b (1.48 g, 2.74 mmol) to form a yellow suspension. At −80° C. an Et$_2$O (5 mL) solution of 2-isopropylphenyllithium (0.690 g, 5.47 mmol) was added dropwise over 5 minutes. Upon the start of the addition the mixture became dark purple. The mixture was allowed to slowly warm to ambient temperature while stirring overnight. Then water was added (30 mL) and the yellow organic layer was separated and dried with brine. Further drying over MgSO$_4$ followed by filtration and evaporation afforded crude diamine 7p as a yellow oil that was found by $^1$H NMR spectroscopy to be contaminated with about 10% of the imine 6b. The product was purified on basic alumina eluted with 5:1 hexanes:dichloromethane, gradually increasing the amount of ethyl acetate to 8%. The product eluted just before the imine impurity. Yield: 1.5 g, 83%. The $^1$H NMR spectrum of 7p in CD$_2$Cl$_2$ solution is complex due to the presence of more than one diastereoisomer.

Synthesis of Pyridyl Diamide Metal Complexes

Shown below in Table 1 are pyridyldiamide complexes. Details of their syntheses are given below. Complexes P-Cl, U-Cl, and V-Cl were prepared as intermediates to P, U, and V, respectively, and were not used directly as catalyst components for olefin polymerizations. Complexes H, P, and V are for comparative purposes.

TABLE 1

Pyridyl diamide complexes used as precatalysts for olefin polymerizations.

| Complex | R$^{11}$ | R$^{12}$ | X |
|---|---|---|---|
| P-Cl* | Ph | 2-iPrPh | Cl |
| U-Cl* | Mes | H | Cl |
| V-Cl* | Mes | 2-iPrPh | Cl |
| H* | Ph | H | Bn |
| P* | Ph | 2-iPrPh | Me |
| U | Mes | H | Me |
| V* | Mes | 2-iPrPh | Me |

*For comparative purposes or prepared as synthetic intermediates.

Complex P-Cl. Benzene (4 mL) was added to 2,6-diisopropyl-N-((2-isopropylphenyl)(6-(2-((phenylamino)methyl)naphthalen-1-yl)pyridin-2-yl)methyl)aniline (7b) (0.254 g, 0.411 mmol) and HfBn$_2$Cl$_2$(OEt$_2$)$_n$ (0.232 g, 0.411 mmol) to give a clear yellow solution. The mixture was heated to 70° C. for 5 hours in the dark. The volatiles were then evaporated and the resulting solid was dried under reduced pressure. The solid was stirred in Et$_2$O (4 mL), collected on a glass frit, and dried under reduced pressure to afford the dichloride derivative P-Cl (0.263 g, 74.0%).

Complex U-Cl. Toluene (8 mL) was added to 7o (0.368 g, 0.680 mmol) and Hf(NMe$_2$)$_2$Cl$_2$(dme) (0.291 g, 0.680 mmol) to form a clear orange solution. The mixture was heated to 70° C. in the dark. After 16 hours white solid had formed as a suspension. The volatiles were evaporated and the solid was suspended in CH$_2$Cl$_2$ (10 mL). The solid was collected on a frit and dried under reduced pressure (0.17 g). The CH$_2$Cl$_2$ solution was evaporated and Et$_2$O (10 mL) was added to the residue. The resulting solid was collected on a frit, washed with CH$_2$Cl$_2$ (5 mL) and dried under reduced pressure. Total yield: 0.26 g, 49%. $^1$H NMR spectroscopy indicates that the solid is fairly pure product U-Cl.

Complex V-Cl. Toluene (6 mL) was added to 7p (0.222 g, 0.336 mmol) and Hf(NMe$_2$)$_2$Cl$_2$(dme) (0.144 g, 0.336 mmol) to form a clear, nearly colorless solution. The mixture was heated to 90° C. in the dark. After 15 hours the volatiles were evaporated and Et$_2$O (5 mL) was added. The resulting very pale yellow solid was collected on a fitted disk and dried under reduced pressure. $^1$H NMR spectroscopic data indicates that the product is >95% a single diastereomer. Yield: 0.076 g, 25%.

Complex H. Benzene (5 mL) was added to HfBn$_4$ (0.171 g, 0.315 mmol) and 2,6-diisopropyl-N-((6-(2-((phenylamino)methyl)naphthalen-1-yl)pyridin-2-yl)methyl)aniline (7a) (0.158 g, 0.315 mmol). The slightly cloudy yellow solution was heated to 50° C. After 4 hours the volatiles were evaporated to give a solid that was extracted with Et$_2$O (20 mL) and filtered. Concentration to 7 mL and cooling to −10° C. overnight afforded yellow crystals (0.12 g) of product that were isolated and dried under reduced pressure. A second crop formed upon concentration and cooling of the mother liquor. Total yield: 0.182 g, 67.3%. $^1$H NMR (500 MHz, C$_6$D$_6$): 8.02 (m, 1H), 7.58 (m, 1H), 7.39 (d, 1H), 6.77-7.25 (m, 19H), 6.64 (m, 2H), 6.47 (m, 3H), 5.52 (d, 2H), 4.74 (AB quartet, Δυ=238 Hz, J=20 Hz), 4.68 (AB quartet, Δυ=402 Hz, J=13 Hz), 3.60 (sept, 1H), 2.01 (sept, 1H), 2.05 (d, 1H), 1.74 (m, 3H), 1.30 (d, 3H), 1.23 (d, 3H), 1.13 (d, 3H), 1.08 (d, 3H).

Complex P. Prepared from P-Cl and Me$_2$Mg in a manner similar to that used for complex U. $^1$H NMR spectroscopic data indicates that the product is >95% a single diastereomer. Yield: 79%. $^1$H NMR (500 MHz, C$_6$D$_6$): 7.6-7.7 (m, 3H), 7.45 (m, 3H), 7.36 (m, 2H), 7.23 (t, 1H), 6.7-7.2 (m, 12H), 6.37 (s, 1H), 4.55 (s, 2H), 3.86 (sept, 1H), 2.75-2.92 (m, 2H), 1.33 (d, 3H), 1.28 (d, 3H), 1.19 (d, 3H), 1.15 (d, 3H), 0.59 (d, 3H), 0.53 (s, 3H), −0.10 (d, 3H), −0.41 (s, 3H).

Complex U. The following reaction was performed while shielded from light. CH$_2$Cl$_2$ (20 mL) was added to U-Cl (0.206 g, 0.255 mmol) to form a very cloudy solution. At −40° C. Me2Mg (0.795 mL, 0.255 mmol) in Et$_2$O was added dropwise over 5 minutes. After stirring for 1 hour the cold bath was removed and the mixture was allowed to warm to ambient temperature. After 30 minutes the volatiles were removed by evaporation and the residue was extracted with CH$_2$Cl$_2$ (10 mL). Filtration afforded a clear yellow solution that was evaporated to a pale yellow solid that was suspended in pentane (10 mL), collected on a glass frit, and dried under reduced pressure. $^1$H NMR spectroscopy indicates the presence of 0.4 equivalents of pentane. Yield: 0.15 g, 76%. $^1$H NMR (500 MHz, CD$_2$-Cl$_2$): 8.06-8.11 (m, 2H), 7.96 (d, 1H), 7.77 (d, 1H), 7.67 (d, 2H), 7.46-7.57 (d, 4H), 6.82-7.10 (m, 5H), 5.05 (AB quartet, Δυ=158 Hz, J=26 Hz), 4.22 (AB quartet, Δυ=296 Hz, J=15 Hz), 3.69 (sept, 1H), 3.03 (sept, 1H), 2.56 (s, 3H), 2.25 (s, 3H), 1.95 (s, 3H), 1.18 (d, 6H), 1.06, (d, 3H), 0.55 (d, 3H), −0.83 (s, 3H), −1.19 (s, 3H).

Complex V. The reaction of V-Cl with Me$_2$Mg was performed analogously to that described for complex U, with the exception that 1.3 equivalents of Me$_2$Mg were used. Complex V was isolated as a pale yellow solid that contained 0.3 equivalents of pentane (by $^1$H NMR spectroscopy). $^1$H NMR spectroscopic data indicates that the product is >95% a single diastereomer. Yield: 73%. $^1$H NMR (500 MHz, $CD_2Cl_2$): 8.13 (d, 1H), 8.01 (d, 1H), 7.95 (t, 1H), 7.82 (d, 1H), 7.62 (d, 1H), 7.57 (t, 1H), 7.52 (t, 1H), 7.34 (d, 1H), 7.13 (d, 1H), 6.72-7.08 (m, 9H), 6.36 (s, 1H), 4.26 (AB quartet, Δυ=288 Hz, J=12 Hz), 3.40 (sept, 1H), 3.26 (sept, 1H), 2.78 (sept, 1H), 2.57 (s, 3H), 2.22 (s, 3H), 1.85 (s, 3H), 1.45 (d, 3H), 1.17 (d, 3H), 0.84 (d, 3H), 0.53 (d, 3H), 0.43 (d, 3H), −0.17 (d, 3H), −0.80 (s, 3H), −0.97 (s, 3H).

Polymerizations Examples

General Polymerization Procedures

Unless stated otherwise propylene homopolymerizations and ethylene-propylene copolymerizations were carried out in a parallel, pressure reactor, as generally described in U.S. Pat. Nos. 6,306,658; 6,455,316; 6,489,168; WO 00/09255; and Murphy et al., J. Am. Chem. Soc., 2003, 125, pages 4306-4317, each of which is fully incorporated herein by reference for US purposes. Although the specific quantities, temperatures, solvents, reactants, reactant ratios, pressures, and other variables are frequently changed from one polymerization run to the next, the following describes a typical polymerization performed in a parallel, pressure reactor.

A pre-weighed glass vial insert and disposable stirring paddle were fitted to each reaction vessel of the reactor, which contains 48 individual reaction vessels. The reactor was then closed and propylene (typically 1 mL) was introduced to each vessel as a condensed gas liquid. If ethylene was added as a comonomer, it was added before the propylene as a gas to a pre-determined pressure (typically 10-80 psi) while the reactor vessels were heated to a set temperature (typically 40° C.). Then solvent (typically isohexane) was added to bring the total reaction volume, including the subsequent additions, to 5 mL and the reactor vessels were heated to their set temperature (usually between 50° C. and 110° C.). At this time scavenger and/or co-catalyst and/or a chain transfer agent, such as tri-n-octylaluminum in toluene (typically 100-1000 nmol) was added.

The contents of the vessel were stirred at 800 rpm. An activator solution (typically 1.0-1.2 molar equivalents of dimethyl anilinium tetrakis-pentafluorophenyl borate dissolved in toluene or 100-1000 molar equivalents of methyl alumoxane (MAO) in toluene) was then injected into the reaction vessel along with 500 microliters of toluene, followed by a toluene solution of catalyst (typically 0.40 mM in toluene, usually 20-40 nanomols of catalyst) and another aliquot of toluene (500 microliters). Equivalence is determined based on the mol equivalents relative to the moles of the transition metal in the catalyst complex.

The reaction was then allowed to proceed until a pre-determined amount of pressure had been taken up by the reaction. Alternatively, the reaction may be allowed to proceed for a set amount of time. At this point, the reaction was quenched by pressurizing the vessel with compressed air. After the polymerization reaction, the glass vial insert containing the polymer product and solvent was removed from the pressure cell and the inert atmosphere glove box, and the volatile components were removed using a Genevac HT-12 centrifuge and Genevac VC3000D vacuum evaporator operating at elevated temperature and reduced pressure. The vial was then weighed to determine the yield of the polymer product. The resultant polymer was analyzed by Rapid GPC (see below) to determine the molecular weight, by FT-IR (see below) to determine percent ethylene incorporation, and by DSC (see below) to determine melting point.

To determine various molecular weight related values by GPC, high temperature size exclusion chromatography was performed using an automated "Rapid GPC" system as generally described in U.S. Pat. Nos. 6,491,816; 6,491,823; 6,475,391; 6,461,515; 6,436,292; 6,406,632; 6,175,409; 6,454,947; 6,260,407; and 6,294,388; each of which is fully incorporated herein by reference for US purposes. This apparatus has a series of three 30 cm×7.5 mm linear columns, each containing PLgel 10 um, Mix B. The GPC system was calibrated using polystyrene standards ranging from 580-3,390,000 g/mol. The system was operated at an eluent flow rate of 2.0 mL/minutes and an oven temperature of 165° C. 1,2,4-trichlorobenzene was used as the eluent. The polymer samples were dissolved in 1,2,4-trichlorobenzene at a concentration of 0.1-0.9 mg/mL. 250 uL of a polymer solution was injected into the system. The concentration of the polymer in the eluent was monitored using an evaporative light scattering detector. The molecular weights presented are relative to linear polystyrene standards and are uncorrected.

Differential Scanning Calorimetry (DSC) measurements were performed on a TA-Q100 instrument to determine the melting point of the polymers. Samples were pre-annealed at 220° C. for 15 minutes and then allowed to cool to room temperature overnight. The samples were then heated to 220° C. at a rate of 100° C./minutes and then cooled at a rate of 50° C./min. Melting points were collected during the heating period. The weight percent of ethylene incorporated in the ethylene-propylene copolymers was determined by rapid FT-IR spectroscopy on a Bruker Equinox 55+ IR in reflection mode. Samples were prepared in a thin film format by evaporative deposition techniques. Weight percent ethylene was obtained from the ratio of peak heights at 744-715 and 1189-1126 $cm^{-1}$. This method was calibrated using a set of ethylene/propylene copolymers with a range of known wt% ethylene content.

Effect of Substitution at $R^{11}$ Position on Propylene Homopolymerization

The effect of substitution at the $R^{11}$ position on propylene polymerization can be determined by comparing the performance of complex U ($R^{11}$=Ph, $R^{12}$=H) to that of H ($R^{11}$=Mes, $R^{12}$=H) when both are activated under identical conditions. The X groups for U and H differ (methyl vs benzyl), but this change has a negligible effect on the polymer produced. Similarly the performance of complex V ($R^{11}$=Mes, $R^{12}$=2-$^i$PrPh) can be compared to that of complex P ($R^{11}$=Ph, $R^{12}$=2-$^i$PrPh) when both are activated under identical conditions. These experiments were performed and the results are shown in Table 2. Comparing runs 13-18 with runs 1-6 it is observed that in under both conditions explored (70 and 100° C.) the catalyst mixture formed from complex U ($R^{11}$=Mes, $R^{12}$=H) was preferred over that formed from complex H ($R^{11}$=H, $R^{12}$=H) in that it produced polypropylene with a much higher (ca., +45° C.) melting point. Additionally, at all temperatures significantly higher molecular weight polypropylene was produced using complex U compared to complex H. Comparing runs 19-24 with runs 7-12 it is observed that in under both conditions explored (70 and 100° C.) the catalyst mixture formed from complex V ($R^{11}$=Mes, $R^{12}$=2-$^i$PrPh) was not preferred over that formed from complex P ($R^{11}$=Ph, $R^{12}$=2-$^i$PrPh) because it had low activity for propylene homopolymerization thus indicating that simultaneously having large groups in the $R^1$, $R^{11}$, and $R^{12}$ positions can be detrimental to catalyst activity.

TABLE 2

Effect of substitution at $R^{11}$ position on propylene polymerization. Conditions: isohexane solvent, propylene added = 1 mL, total volume = 5 mL, N,N-dimethylanilinium tetrakis(pentafluorophenyl)borate activator (11 equivalent), tri-n-octylaluminum (300 nmol).

| run | complex | Polym. T (° C.) | Catalyst (mmol) | activity* | Mw (g/mol) | Mn (g/mol) | Mw/Mn | Tm* (° C.) |
|---|---|---|---|---|---|---|---|---|
| 1 | H | 70 | 0.00008 | 71,060 | 650,608 | 417,538 | 1.6 | 107.3 |
| 2 | H | 70 | 0.00008 | 75,206 | 522,409 | 323,176 | 1.6 | 107.9 |
| 3 | H | 70 | 0.00008 | 79,192 | 597,601 | 392,869 | 1.5 | 106.3 |
| 4 | H | 100 | 0.00008 | 83,059 | 149,835 | 100,050 | 1.5 | 101.8 |
| 5 | H | 100 | 0.00008 | 68,308 | 151,593 | 100,799 | 1.5 | 103.5 |
| 6 | H | 100 | 0.00008 | 68,358 | 156,601 | 101,056 | 1.5 | 105.3 |
| 7 | P | 70 | 0.00006 | 83,747 | 542,445 | 324,920 | 1.7 | 149.9 |
| 8 | P | 70 | 0.00006 | 63,880 | 677,583 | 410,223 | 1.7 | 150.5 |
| 9 | P | 70 | 0.00006 | 55,525 | 606,728 | 369,906 | 1.6 | 150.1 |
| 10 | P | 100 | 0.00006 | 29,983 | 79,722 | 48,532 | 1.6 | 145.6 |
| 11 | P | 100 | 0.00006 | 28,565 | 88,107 | 51,916 | 1.7 | 145.9 |
| 12 | P | 100 | 0.00006 | 10,278 | 79,091 | 47,911 | 1.7 | 145.0 |
| 13 | U | 70 | 0.00006 | 69,941 | 938,797 | 581,245 | 1.6 | 151.9 |
| 14 | U | 70 | 0.00006 | 62,052 | 978,043 | 608,854 | 1.6 | 152.9 |
| 15 | U | 70 | 0.00006 | 61,495 | 933,924 | 567,923 | 1.6 | 152.3 |
| 16 | U | 100 | 0.00006 | 11,805 | 306,500 | 185,609 | 1.7 | 149.3 |
| 17 | U | 100 | 0.00006 | 14,752 | 301,453 | 184,977 | 1.6 | 148.9 |
| 18 | U | 100 | 0.00006 | 19,602 | 293,794 | 170,366 | 1.7 | 148.9 |
| 19 | V | 70 | 0.00006 | 223 | n.d. | n.d. | n.d. | n.d. |
| 20 | V | 70 | 0.00006 | 200 | n.d. | n.d. | n.d. | n.d. |
| 21 | V | 70 | 0.00006 | 186 | n.d. | n.d. | n.d. | n.d. |
| 22 | V | 100 | 0.00006 | 50 | n.d. | n.d. | n.d. | n.d. |
| 23 | V | 100 | 0.00006 | 40 | n.d. | n.d. | n.d. | n.d. |
| 24 | V | 100 | 0.00006 | 83 | n.d. | n.d. | n.d. | n.d. |

*Activity is given in g of polymer/mmol catalyst/hour; Tm is the first melt temperature given in degrees Celsius.
"n.d." means not determined.

Effect of Substitution at $R^{11}$ Position on Ethylene-Propylene Copolymerization The effect of substitution at the $R^{11}$ position on ethylene-propylene copolymerization can be determined by comparing the performance of complex U ($R^{11}$=Ph, $R^{12}$=H) to that of H ($R^{11}$=Mes, $R^{12}$=H) when both are activated under identical conditions. The X groups for U and H differ (methyl vs benzyl), but this change has a negligible effect on the polymer produced. These experiments were performed and the results are shown in Table 3. Comparing runs 13-24 with runs 1-12 it is observed that the catalyst mixture formed from complex U ($R^{11}$=Mes, $R^{12}$=H) was preferred over that formed from complex H ($R^{11}$=H, $R^{12}$=H) because, inter alia: (i) it produced higher molecular weight ethylene-polypropylene copolymer; (ii) it has higher activity; and (iii) it enabled the production of ethylene-propylene copolymers containing low (i.e., less than 35%) amounts of ethylene.

TABLE 3

Effect of substitution at $R^{11}$ position on ethylene-propylene copolymerization. Conditions: 70° C., isohexane solvent, propylene added = 1 mL, total volume = 5 mL, catalyst = 20 nmol, N,N-dimethylanilinium tetrakis(pentafluorophenyl)borate activator (11 equivalent), tri-n-octylaluminum (300 nmol).

| run | complex | ethylene (psi) | activity* | wt % ethylene | Mw (g/mol) | Mn (g/mol) | Mw/Mn | Tm* (° C.) | delta $H_f$ (J/g) |
|---|---|---|---|---|---|---|---|---|---|
| 1 | H | 0 | 3,939 | 0 | 196,850 | 114,948 | 1.7 | 114.3 | 42.4 |
| 2 | H | 0 | 5,241 | 0 | 275,782 | 157,632 | 1.7 | 114.1 | 40.6 |
| 3 | H | 10 | 7,698 | 38 | 191,209 | 120,137 | 1.6 | n.d. | n.d. |
| 4 | H | 10 | 23,966 | 40 | 231,495 | 143,199 | 1.6 | n.d. | n.d. |
| 5 | H | 20 | 19,030 | n.d. | 193,124 | 127,193 | 1.5 | n.d. | n.d. |
| 6 | H | 20 | 23,233 | n.d. | 211,981 | 136,659 | 1.6 | n.d. | n.d. |
| 7 | H | 40 | 35,296 | n.d. | 204,196 | 136,164 | 1.5 | n.d. | n.d. |
| 8 | H | 40 | 30,658 | n.d. | 220,537 | 146,213 | 1.5 | n.d. | n.d. |
| 9 | H | 60 | 33,390 | n.d. | 216,808 | 146,807 | 1.5 | n.d. | n.d. |
| 10 | H | 60 | 45,052 | n.d. | 243,929 | 163,572 | 1.5 | n.d. | n.d. |
| 11 | H | 80 | 51,708 | n.d. | 222,632 | 154,338 | 1.4 | n.d. | n.d. |
| 12 | H | 80 | 56,561 | n.d. | 266,260 | 180,590 | 1.5 | n.d. | n.d. |
| 13 | U | 0 | 104,920 | 0 | 1,032,822 | 689,616 | 1.5 | 153.1 | 96.2 |
| 14 | U | 0 | 99,799 | 0 | 1,172,412 | 786,343 | 1.5 | 152.3 | 74.1 |
| 15 | U | 10 | 159,658 | 12 | 1,010,324 | 651,380 | 1.6 | 105.3 | 16.0 |
| 16 | U | 10 | 171,298 | 13 | 1,156,409 | 775,068 | 1.5 | 110.9 | 25.2 |
| 17 | U | 20 | 199,957 | 19 | 1,015,492 | 652,743 | 1.6 | 99.0 | 16.0 |
| 18 | U | 20 | 245,581 | 20 | 1,120,847 | 740,541 | 1.5 | 104.7 | 9.6 |
| 19 | U | 40 | 281,842 | 27 | 997,230 | 679,958 | 1.5 | n.d. | n.d. |
| 20 | U | 40 | 321,244 | 26 | 1,242,981 | 833,026 | 1.5 | n.d. | n.d. |
| 21 | U | 60 | 628,841 | 41 | 1,068,755 | 695,293 | 1.5 | n.d. | n.d. |

TABLE 3-continued

Effect of substitution at $R^{11}$ position on ethylene-propylene copolymerization.
Conditions: 70° C., isohexane solvent, propylene added = 1 mL, total volume = 5 mL,
catalyst = 20 nmol, N,N-dimethylanilinium tetrakis(pentafluorophenyl)borate activator
(11 equivalent), tri-n-octylaluminum (300 nmol).

| run | complex | ethylene (psi) | activity* | wt % ethylene | Mw (g/mol) | Mn (g/mol) | Mw/Mn | Tm* (° C.) | delta $H_f$ (J/g) |
|---|---|---|---|---|---|---|---|---|---|
| 22 | U | 60 | 455,732 | 38 | 1,261,041 | 838,804 | 1.5 | n.d. | n.d. |
| 23 | U | 80 | 815,178 | 44 | 1,062,270 | 707,770 | 1.5 | n.d. | n.d. |
| 24 | U | 80 | 692,083 | 47 | 1,369,389 | 885,855 | 1.5 | n.d. | n.d. |

*Activity is given in g of polymer/mmol catalyst/hour; Tm is the first melt temperature given in degrees Celsius.
"n.d." means not determined.

For purposes of the claims, the following test methods shall be used.

$^1$H NMR $^1$H NMR data is collected at 120° C. shall be used in a 5 mm probe using a spectrometer with a $^1$H frequency of at least 400 MHz. Data is recorded using a maximum pulse width of 45°, 8 seconds between pulses and signal averaging 120 transients. Spectral signals are integrated. Samples are dissolved in deuterated methylene chloride at concentrations between 10 wt % to 15 wt % prior to being inserted into the spectrometer magnet. Prior to data analysis, spectra are referenced by setting the residual CHDCl$_2$ resonance to 5.24 ppm.

$^{13}$C NMR $^{13}$C NMR data is collected at 120° C. using a spectrometer with a $^{13}$C frequency of at least 75 MHz. A 90 degree pulse, an acquisition time adjusted to give a digital resolution between 0.1 and 0.12 Hz, at least a 10 second pulse acquisition delay time with continuous broadband proton decoupling using swept square wave modulation without gating is employed during the entire acquisition period. The spectra are acquired with time averaging to provide a signal to noise level adequate to measure the signals of interest. Samples are dissolved in deuterated methylene chloride at concentrations between 10 wt % to 15 wt % prior to being inserted into the spectrometer magnet. Prior to data analysis, spectra are referenced by setting the chemical shift of the deuterated methylene chloride solvent signal to 54 ppm.

All documents described herein are incorporated by reference herein for purposes of all jurisdictions where such practice is allowed, including any priority documents and/or testing procedures to the extent they are not inconsistent with this text, provided however that any priority document not named in the initially filed application or filing documents is NOT incorporated by reference herein. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law. Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

What is claimed is:

1. A pyridyldiamido transition metal complex represented by the formula: (I) or (II):

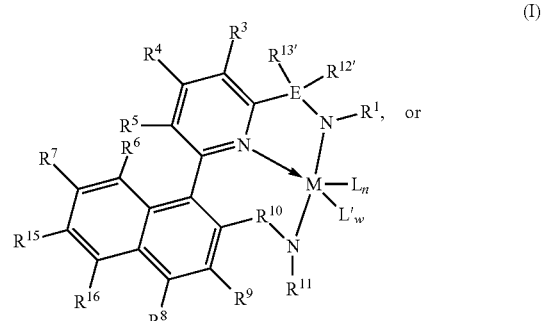
(I)

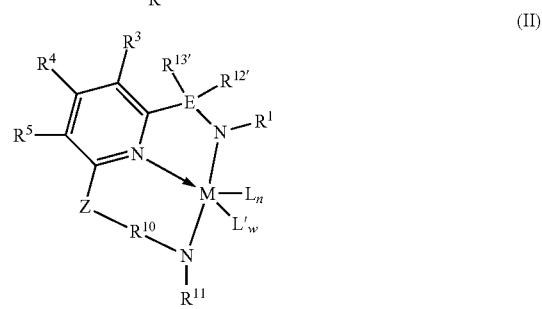
(II)

wherein:

M is a Group 3, 4, 5, 6, 7, 8, 9, 10, 11, or 12 metal;

$R^1$ is selected from the group consisting of hydrocarbyls, substituted hydrocarbyls, and silyl groups;

$R^{11}$ is selected from the group consisting of substituted 5 or 6 membered aromatic rings;

$R^{10}$ is -E*($R^{12}$)($R^{13}$)—;

E and E* are, independently, carbon, silicon, or germanium;

each $R^{12}$ and $R^{13}$ is independently selected from the group consisting of hydrogen, hydrocarbyl, substituted hydrocarbyl, alkoxy, silyl, amino, aryloxy, halogen, and phosphino, $R^{12}$ and $R^{13}$ may be joined to form a saturated, substituted or unsubstituted hydrocarbyl ring, where the ring has 4, 5, 6, or 7 ring carbon atoms and where substitutions on the ring can join to form additional rings, or $R^{12}$ and $R^{13}$ may be joined to form a saturated heterocyclic ring, or a saturated substituted heterocyclic ring where substitutions on the ring can join to form additional rings;

each $R^{12}$* and $R^{13}$* is independently selected from the group consisting of hydrogen, C1 to C5 hydrocarbyls, and substituted C1 to C5 hydrocarbyls;

$R^3$, $R^4$, and $R^5$ are independently selected from the group consisting of hydrogen, hydrocarbyls, substituted hydrocarbyls, alkoxy, aryloxy, halogen, amino, and silyl, and wherein adjacent R groups ($R^3$ & $R^4$ and/or $R^4$ & $R^5$) may be joined to form a substituted or unsubstituted hydrocarbyl or heterocyclic ring, where the ring has 5, 6, 7, or 8 ring atoms and where substitutions on the ring can join to form additional rings;

$R^6$, $R^7$, $R^8$, $R^9$, $R^{15}$, and $R^{16}$ are independently selected from the group consisting of hydrogen, hydrocarbyls, substituted hydrocarbyls, alkoxy, halogen, amino, and silyl, and the pairs of positions, and wherein adjacent R groups ($R^6$ & $R^7$, and/or $R^7$ & $R^{15}$, and/or $R^{16}$ & $R^{15}$, and/or $R^8$ & $R^9$) may be joined to form a saturated, substituted or unsubstituted hydrocarbyl or heterocyclic ring, where the ring has 5, 6, 7, or 8 ring carbon atoms and where substitutions on the ring can join to form additional rings;

L is an anionic leaving group, where the L groups may be the same or different and any two L groups may be linked to form a dianionic leaving group;

n is 0, 1, 2, 3, or 4;

L' is neutral Lewis base;

w is 0, 1, 2, 3, or 4;

Z is —$(R^{14*})_p$Q-J$(R^{15*})_q$— where Q or J is bonded to $R^{10}$;

J is C or Si;

Q is C, N, or Si;

$R^{14*}$ and $R^{15*}$ are independently selected from the group consisting of hydrogen, hydrocarbyls, and substituted hydrocarbyls, and wherein adjacent $R^{14*}$ and $R^{15*}$ groups may be joined to form an aromatic or saturated, substituted or unsubstituted hydrocarbyl ring, where the ring has 5, 6, 7, or 8 ring carbon atoms and where substitutions on the ring can join to form additional rings;

p is 1 or 2; and q is 1 or 2.

2. The complex of claim 1, wherein M is Ti, Zr, or Hf

3. The complex of claim 1, wherein $R^{10}$ is represented by the formula:

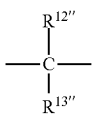

where $R^{12''}$ is hydrogen, alkyl, aryl, or halogen; and $R^{13''}$ is hydrogen, alkyl, aryl, or halogen.

4. The complex of claim 1, wherein $R^6$, $R^7$, $R^8$, $R^9$, $R^{15}$, and $R^{16}$ are independently selected from the group consisting of hydrogen, hydrocarbyls, substituted hydrocarbyls, alkoxy, halogen, amino, and silyl.

5. The complex of claim 1, wherein $R^1$, $R^3$, $R^4$, and $R^5$ each contain no more than 30 carbon atoms.

6. The complex of claim 4, wherein $R^1$, $R^3$, $R^4$, $R^5$, $R^6$, $R^7$, $R^8$, $R^9$, and $R^{15}$ each contain no more than 30 carbon atoms.

7. The complex of claim 1, wherein E and E* are carbon and $R^1$ is selected from phenyl groups that are substituted with 0, 1, 2, 3, 4, or 5 substituents selected from the group consisting of F, Cl, Br, I, $CF_3$, $NO_2$, alkoxy, dialkylamino, hydrocarbyl, and substituted hydrocarbyls groups with from one to ten carbons.

8. The complex of claim 1, wherein each L is independently selected from the group consisting of halide, alkyl, aryl, alkoxy, amido, hydrido, phenoxy, hydroxy, silyl, allyl, alkenyl, triflate, alkylsulfonate, arylsulfonate, and alkynyl;

and each L' is independently selected from the group consisting of ethers, thio-ethers, amines, nitriles, imines, pyridines, and phosphines.

9. The complex of claim 1, wherein both $R^{12}$ and $R^{13}$ are a $C_1$ to $C_{100}$ alkyl group.

10. The complex of claim 1, wherein the complex is represented by formula (I).

11. The complex of claim 1, wherein the complex is represented by formula (II).

12. The complex of claim 1, wherein $R^{12*}$ and $R^{13*}$ are the same.

13. The complex of claim 1, wherein the complex is represented by formula (I) and $R^{12*}$ is H, $R^{13*}$ is a group containing from 1 to 5 carbons, M is a Group 4 metal, E is carbon and $R^{10}$ is $CH_2$.

14. The complex of claim 1, wherein the complex is represented by formula (II) and $R^{12*}$ is a group containing from 1 to 5 carbons, M is a Group 4 metal, E is carbon and $R^{10}$ is $CH_2$.

15. The complex of claim 1, wherein M is a Group 4 metal, E* is carbon and $R^{10}$ is $CH_2$.

16. The complex of claim 1, wherein $R^{11}$ is selected from the group consisting of substituted 6 membered aromatic rings.

17. The complex of claim 1, wherein $R^{11}$ is selected from the group consisting of substituted 5 or 6 membered rings where the ring atoms are carbon or heterocyclic rings having 1, 2 or 3 heteroatoms in the ring and where the substitution is a hydrocarbyl group, a heteroatom, or a heteroatom containing group.

18. The complex of claim 1, wherein $R^{11}$ is a substituted aryl group.

19. The complex of claim 1, wherein $R^{11}$ is a 2,6 or 2,4,6 substituted aryl group.

20. The complex of claim 1, wherein $R^{11}$ is a 2,6 or 2,4,6 substituted aryl, where the substituents are methyl, ethyl, methoxy, propyl, tert-butyl, butyl, isopropyl, pentyl, hexyl, isobutyl, chloro, fluoro, bromo, iodo, trimethylsilyl, or triethylsilyl.

21. The complex of claim 1, wherein $R^{11}$ is 2,4,6-trimethylphenyl, 2,6-dimethylphenyl, 2,6-diethylphenyl, 2,6-diisobutylphenyl, 2,5-dimethylphenyl, 2,4,5-trimethylphenyl, 2,3,4,5,6-pentamethylphenyl, 2,6-diisopropylphenyl, or 2,4,6-triisopropylphenyl.

22. A process for preparing the pyridyldiamido complex of claim 2 comprising reaction of a pyridyldiamine with a group 4 transition metal complex of the general formula $MY_2L_2L'_w$, where M is Ti, Zr, or Hf, Y is a deprotonated amine or hydrocarbanion group; L is an anionic leaving group, where the L and Y groups may be the same or different and any two L and/or Y groups may be linked to form a dianionic group; L' is neutral Lewis base; and w is 0, 1, 2, 3, or 4.

23. A catalyst system comprising an activator and the complex of claim 1.

24. The catalyst system of claim 23, wherein the activator is an alumoxane.

25. The catalyst system of claim 23, wherein the activator is a non-coordinating anion.

26. A polymerization process comprising a) contacting one or more alkene monomers with a catalyst system comprising: i) an activator and ii) the pyridyldiamido transition metal complex of claim 1.

27. The process of claim 26, wherein the activator is an alumoxane.

28. The process of claim 26, wherein the activator is a non-coordinating anion.

29. The process of claim 26, wherein the monomer comprises ethylene.

30. The process of claim 26, wherein the monomer comprises propylene.

31. The process of claim 26, wherein the pyridyldiamido transition metal complex is supported.

32. The process of claim 26, wherein $R_6$, $R_7$, $R_8$, and $R_9$ are independently selected from the group consisting of hydrogen, hydrocarbyls, substituted hydrocarbyls, alkoxy, halogen, amino, and silyl.

33. The process of claim 26, wherein $R^{11}$ is selected from the group consisting of substituted 5 or 6 membered rings where the ring atoms are carbon or heterocyclic rings having 1, 2 or 3 heteroatoms in the ring and where the substitution is a hydrocarbyl group, a heteroatom, or a heteroatom containing group.

34. The process of claim 26, wherein $R^{11}$ is a 6 membered ring.

35. The process of claim 26, wherein $R^{11}$ is a 2,6 or 2,4,6 substituted aryl, where the substituents are methyl, ethyl, methoxy, propyl, tert-butyl, butyl, isopropyl, pentyl, hexyl, isobutyl, chloro, fluoro, bromo, iodo, trimethylsilyl, or triethylsilyl.

* * * * *